United States Patent
Matsuhisa et al.

(10) Patent No.: US 12,065,276 B2
(45) Date of Patent: Aug. 20, 2024

(54) WOUND BODY, CORE BODY FOR WOUND BODY, COMBINATION OF WOUND BODY AND SUPPORT SHAFT, AND COMBINATION OF WOUND BODY AND MEDICAL PACKING APPARATUS

(71) Applicant: Takazono Corporation, Osaka (JP)

(72) Inventors: Yoshiki Matsuhisa, Osaka (JP); Yoshiyuki Michihata, Osaka (JP); Tomohiro Yoshimura, Osaka (JP); Shinji Iwasaki, Osaka (JP); Akihiro Nakamura, Osaka (JP)

(73) Assignee: Takazono Corporation, Kadoma (JP)

( * ) Notice: Subject to any disclaimer, the term of this patent is extended or adjusted under 35 U.S.C. 154(b) by 362 days.

(21) Appl. No.: 17/613,364

(22) PCT Filed: Apr. 20, 2021

(86) PCT No.: PCT/JP2021/015943
§ 371 (c)(1),
(2) Date: Nov. 22, 2021

(87) PCT Pub. No.: WO2021/215415
PCT Pub. Date: Oct. 28, 2021

(65) Prior Publication Data
US 2022/0219852 A1 Jul. 14, 2022

(30) Foreign Application Priority Data

Apr. 24, 2020 (JP) .................................. 2020-077411
Apr. 24, 2020 (JP) .................................. 2020-077431
(Continued)

(51) Int. Cl.
*B65B 41/16* (2006.01)
*A61B 50/30* (2016.01)
*B65B 1/02* (2006.01)
(Continued)

(52) U.S. Cl.
CPC .............. *B65B 41/16* (2013.01); *A61B 50/30* (2016.02); *B65B 1/02* (2013.01); *B65B 35/12* (2013.01);
(Continued)

(58) Field of Classification Search
CPC .. B65H 75/30; B65H 75/10; B65H 2701/512; B65H 18/28; B65H 19/2276; B65H 75/18; B65B 41/10; A61B 50/30
See application file for complete search history.

(56) References Cited

U.S. PATENT DOCUMENTS

| 4,325,569 A | 4/1982 | Suzuki et al. |
| 2002/0134057 A1 | 9/2002 | Haraguchi |

(Continued)

FOREIGN PATENT DOCUMENTS

| CN | 101544136 A | 9/2009 |
| JP | 65644757 U | 4/1981 |

(Continued)

Primary Examiner — Veronica Martin
(74) Attorney, Agent, or Firm — The Webb Law Firm

(57) ABSTRACT

A support shaft capable of supporting a wound body with a long sheet wound therearound includes a first projection located at a proximal end of an outer peripheral part, and a second projection located at a distal end of the outer peripheral part. A core body of the wound body includes a one-end-side first recess part located at one end of an inner peripheral part, an other-end-side firsts recess part located at an other end of the inner peripheral part, and a second recess part located to extend from the one end to the other end. In a state where the core body is mounted on an outer periphery of the support shaft, the first projection engages the one-end-side first recess part or the other-end-side first recess part. When the core body is mounted to the outer periphery of the support shaft, the second projection engages the second recess to allow the circumferential position of the first projection to be aligned with the circumferential posi- (Continued)

tion of the one-end-side first recess part or the other-end-side first recess part around a central axis.

21 Claims, 19 Drawing Sheets

(30) Foreign Application Priority Data

Apr. 28, 2020 (JP) .................................. 2020-078881
Apr. 28, 2020 (JP) .................................. 2020-078895

(51) Int. Cl.
  *B65B 35/12* (2006.01)
  *B65B 51/10* (2006.01)
  *B65D 65/40* (2006.01)

(52) U.S. Cl.
  CPC .............. *B65B 51/10* (2013.01); *B65D 65/40* (2013.01); *B65B 2051/105* (2013.01)

(56) References Cited

U.S. PATENT DOCUMENTS

2003/0080238 A1* 5/2003 Seybold .................. B41J 15/02
                                                           242/611.2
2009/0242603 A1    10/2009 Kobayashi et al.

FOREIGN PATENT DOCUMENTS

| JP | S5644757 Y   | 10/1981 |
| JP | H839912 A    | 2/1996  |
| JP | 2001224663 A | 8/2001  |
| JP | 2009227469 A | 10/2009 |
| JP | 2011189997 A | 9/2011  |
| JP | 2012246015 A | 12/2012 |
| JP | 6613004 B1   | 11/2019 |

* cited by examiner

WOUND BODY, CORE BODY FOR WOUND BODY, COMBINATION OF WOUND BODY AND SUPPORT SHAFT, AND COMBINATION OF WOUND BODY AND MEDICAL PACKING APPARATUS

CROSS REFERENCE TO RELATED APPLICATIONS

This application is the United States national phase of International Application No. PCT/JP2021/015943 filed Apr. 20, 2021, and claims priority to Japanese Patent Application Nos. 2020-77411 and 2020-77431, filed Apr. 24, 2020, and 2020-78881 and 2020-78895, filed Apr. 28, 2020, the disclosures of which are hereby incorporated by reference in their entirety.

BACKGROUND OF THE INVENTION

Field of the Invention

The present invention relates to a wound body formed by winding a packing material in a roll shape that is a strip-shaped sheet, a core body for a wound body that forms the wound body, a combination of the wound body and a support shaft configured to support the wound body, and a combination of the wound body and a medicine packing apparatus configured to pack a medicine using the packing material.

Description of Related Art

There is a medicine packing apparatus configured to pack a medicine using a packing material in the form of a strip-shaped sheet. JP-U S56-44757 B describes an example of a support device for the packing material included in such a medicine packing apparatus. The configuration described in the aforesaid publication includes a mounting base (referred to as "apparatus body" in Patent Literature 1, the following descriptions in parenthesis are the same), and a support shaft (feeding drum) extending therefrom, in which the support shaft is rotatably supported by the mounding base. A core body (core cylinder) is mounted on an outer periphery of the support shaft. A packing material (packing paper) is wound around the outer periphery of the core body to form a roll-shaped wound body. Packing of a medicine can be made for the packing material sequentially drawn out from the wound body.

CITATION LIST

Patent Literature

Patent Literature 1: JP-U S56-44757 B

SUMMARY OF THE INVENTION

For the wound body described in the aforementioned publication, a configuration for aligning the circumferential position of the wound body relative to the support shaft is not included. Meanwhile, since the wound body with the packing material wound therearound is relatively heavy. Thus, there was a difficulty for an operator in aligning the circumferential position of the wound body relative to the support shaft.

It is an object of the present invention to provide a wound body, a core body for wound body, a combination of the wound body and a support shaft, and a combination of the wound body and a medicine packing apparatus that are able to facilitate the mounting operation of the wound body to the support shaft.

According to the present invention, there is provided a wound body formed by winding a long sheet, wherein the wound body is supportable by a support shaft, the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the wound body includes a core body having a cylindrical shape, and the long sheet wound around an outer periphery of the core body, the core body includes a cylindrical inner peripheral part having one end and an other end, the inner peripheral part includes a one-end-side first recess part located at the one end and recessing outward in the radial direction, an other-end-side first recess part located at the other end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the one-end-side first recess part and the other-end-side first recess part, the core body is mountable on the outer periphery of the support shaft from the one end side of the core body or the other end side of the core body, and from the distal end side of the support shaft, the support shaft and the core body are integrally rotatable around the central axis by engagement of the first projection with the one-end-side first recess part or the other-end-side first recess part in a state where the core body is mounted on the outer periphery of the support shaft, and the circumferential position of the first projection around the central axis is aligned with the circumferential position of the one-end side first recess part or the other-end-side first recess part around the central axis by the engagement of the second projection with the second recess part when the core body is mounted on the outer periphery of the support shaft.

According to the present invention, there is further provided a wound body formed by winding a long sheet, including: a core body having a cylindrical shape, and the long sheet wound around an outer periphery of the core body, wherein the core body includes a cylindrical inner peripheral part having one end and an other end, and the inner peripheral part includes a one-end-side first recess part located at the one end and recessing outward in a radial direction, an other-end-side first recess part located at the other end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the one-end-side first recess part and the other-end-side first recess part.

According to the present invention, there is further provided a core body for wound body that is used for a wound body formed by winding a long sheet, wherein the wound body is supportable by a support shaft, the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the core body for the wound body has a cylindrical shape, is configured to allow the long sheet to be wound around an outer periphery of the core body, and includes a cylindrical inner peripheral part having one end and an other end, the inner peripheral part includes an one-end-side first recess part located at the one end and recessing outward in the radial direction, an other-end-side first recess part located at the other end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the one-end-side first recess part and the other-end-side first recess part, the core body for wound body is mountable on the outer periphery of the support shaft from the one end side of the core body for wound body or the other end side of the core body for wound body, and from the distal end side of the support shaft, the support shaft and the core body for wound body are integrally rotatable around the central axis by engagement of the first projection with the one-end-side first recess part or the other-end-side first recess part in a state where the core body for wound body is mounted on the outer periphery of the support shaft, and the circumferential position of the first projection around the central axis is aligned with the circumferential position of the one-end side first recess part or the other-end-side first recess part around the central axis by the engagement of the second projection with the second recess part when the core body for wound body is mounted on the outer periphery of the support shaft.

According to the present invention, there is further provided a combination of a wound body and a support shaft, the combination including a wound body formed by winding a long sheet, and a support shaft that supports the wound body, wherein the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the wound body includes a core body having a cylindrical shape, and the long sheet wound around an outer periphery of the core body, the core body includes a cylindrical inner peripheral part having one end and an other end, the inner peripheral part includes a one-end-side first recess part located at the one end and recessing outward in the radial direction, an other-end-side first recess part located at the other end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the one-end-side first recess part and the other-end-side first recess part, the core body is mountable on the outer periphery of the support shaft from the one end side of the core body or the other end side of the core body, and from the distal end side of the support shaft, the support shaft and the core body are integrally rotatable around the central axis by the engagement of the first projection with the one-end-side first recess part or the other-end-side first recess part in a state where the core body is mounted on the outer periphery of the support shaft, and the circumferential position of the first projection around the central axis is aligned with the circumferential position of the one-end side first recess part or the other-end-side first recess part around the central axis by the engagement of the second projection with the second recess part when the core body is mounted on the outer periphery of the support shaft.

According to the present invention, there is further provided a combination of a wound body and a medicine packing apparatus, the combination including a wound body formed by winding a long sheet, and a medicine packing apparatus that includes a support shaft for supporting the wound body, and that is configured to pack a medicine using the long sheet wound off from the wound body supported by the support shaft, wherein the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the wound body includes a core body having a cylindrical shape, and the long sheet wound around an outer periphery of the core body, the core body includes a cylindrical inner peripheral part having one end and an other end, the inner peripheral part includes a one-end-side first recess part located at the one end and recessing outward in the radial direction, an other-end-side first recess part located at the other end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the one-end-side first recess part and the other-end-side first recess part, the core body is mountable on the outer periphery of the support shaft from the one end side of the core body or the other end side of the core body, and from the distal end side of the support shaft, the support shaft and the core body are integrally rotatable around the central axis by the engagement of the first projection with the one-end-side first recess part or the other-end-side first recess part in a state where the core body is mounted on the outer periphery of the support shaft, and the circumferential position of the first projection around the central axis is aligned with the circumferential position of the one-end-side first recess part or the other-end-side first recess part around the central axis by the engagement of the second projection with the second recess part when the core body is mounted on the outer periphery of the support shaft.

According to the present invention, there is provided a wound body formed by winding a long sheet, wherein the wound body is supportable by a support shaft, the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the wound body includes a core body having a cylindrical shape, and the long sheet wound around an outer periphery of the core body, the core body includes a cylindrical inner peripheral part having one end and an other end, the inner peripheral part includes a first recess part located at the one end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the first recess part, the core body is mountable on the outer periphery of the support shaft from the one end side of the core body and from the distal end side of the support shaft, the support shaft and the core body are integrally rotatable around the central axis by the engagement of the first projection with the first recess part in a state where the core body is mounted on the outer periphery of the support shaft, the circumferential position of the first projection around the central axis is aligned with the circumferential position of the first recess part around the central axis by the engagement of the second projection with the second recess part when the core body is mounted on the outer periphery of the support shaft, and the second recess part includes a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part includes a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the outer peripheral part of the support shaft includes a third projection that is located at an intermediate position between the proximal end of the support shaft and the distal end of the support shaft and that projects outward in the radial direction, the third projection is located at the same position as the second projection in the circumferential direction around the central axis, a projecting amount of the third projection projecting outward in the radial direction with respect to the outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

According to the present invention, there is further provided a core body for wound body that is used for a wound body formed by winding a long sheet, wherein the wound body is supportable by a support shaft, the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the core body for the wound body has a cylindrical shape, is configured to allow the long sheet to be wound around an outer periphery of the core body, and includes a cylindrical inner peripheral part having one end and an other end, the inner peripheral part includes a first recess part located at the one end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the first recess part, the core body for wound body is mountable on the outer periphery of the support shaft from the one end side of the core body for wound body and from the distal end side of the support shaft, the support shaft and the core body for wound body are integrally rotatable around the central axis by the engagement of the first projection with the first recess part in a state where the core body for wound body is mounted on the outer periphery of the support shaft, the circumferential position of the first projection around the central axis is aligned with the circumferential position of the first recess part around the central axis by the engagement of the second projection with the second recess part when the core body for wound body is mounted on the outer periphery of the support shaft, the second recess part includes a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part includes a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the outer peripheral part of the support shaft includes a third projection that is located at an intermediate position between the proximal end of the support shaft and the distal end of the support shaft and that projects outward in the radial direction, the third projection is located at the same position as the second projection in the circumferential direction around the central axis, a projecting amount of the third projection projecting outward in the radial direction with respect to the outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

According to the present invention, there is further provided a combination of a wound body and a support shaft, the combination including a wound body formed by winding a long sheet, and a support shaft that supports the wound body, wherein the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the wound body includes a core body having a cylindrical shape, and the long sheet wound around an outer periphery of the core body, the core body includes a cylindrical inner peripheral part having one end and an other end, the inner peripheral part includes a first recess part located at the one end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the first recess part, the core body is mountable on the outer periphery of the support shaft from the one end side of the core body and from the distal end side of the support shaft, the support shaft and the core body are integrally rotatable around the central axis by engagement of the first projection with the first recess part in a state where the core body is mounted on the outer periphery of the support shaft, the circumferential position of the first projection around the central axis is aligned with the circumferential position of the first recess part around the central axis by the engagement of the second projection with the second recess part when the core body is mounted on the outer periphery of the support shaft, the second recess part includes a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part includes a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the outer peripheral part of the support shaft includes a third projection that is located at an intermediate position between the proximal end of the support shaft and the distal end of the support shaft and that projects outward in the radial direction, the third projection is located at the same position as the second projection in the circumferential direction around the central axis, a projecting amount of the third projection projecting outward in the radial direction with respect to the outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

According to the present invention, there is further provided a combination of a wound body and a medicine packing apparatus, the combination including a wound body formed by winding a long sheet, and a medicine packing apparatus that includes a support shaft for supporting the wound body, and that is configured to pack a medicine using the long sheet wound off from the wound body supported by the support shaft, wherein the support shaft includes a cylindrical outer peripheral part having a proximal end and a distal end, and is configured to be rotatable around a central axis of the outer peripheral part, the outer peripheral part includes a first projection located at the proximal end and projecting outward in a radial direction, and a second projection located at the distal end and projecting outward in the radial direction, in which a projecting amount of the second projection projecting outward in the radial direction with respect to the outer peripheral part is smaller than that of the first projection, the wound body includes a core body having a cylindrical shape, and the long sheet wound around an outer periphery of the core body, the core body includes a cylindrical inner peripheral part having one end and an other end, the inner peripheral part includes a first recess part located at the one end and recessing outward in the radial direction, and a second recess part located to extend from the one end to the other end and recessing outward in the radial direction, in which a recessing amount of the second recess part recessing outward in the radial direction with respect to the inner peripheral part is smaller than that of the first recess part, the core body is mountable on the outer periphery of the support shaft from the one end side of the core body and from the distal end side of the support shaft, the support shaft and the core body are integrally rotatable around the central axis by engagement of the first projection with the first recess part in a state where the core body is mounted on the outer periphery of the support shaft, the circumferential position of the first projection around the central axis is aligned with the circumferential position of the first recess part around the central axis by engagement of the second projection with the second recess part when the core body is mounted on the outer periphery of the support shaft, the second recess part includes a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part includes a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the outer peripheral part of the support shaft includes a third projection that is located at an intermediate position between the proximal end of the support shaft and the distal end of the support shaft, and that projects outward in the radial direction, the third projection is located at the same position as the second projection in the circumferential direction around the central axis, a projecting amount of the third projection projecting outward in the radial direction with respect to the outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

DESCRIPTION OF THE INVENTION

Figure 1:
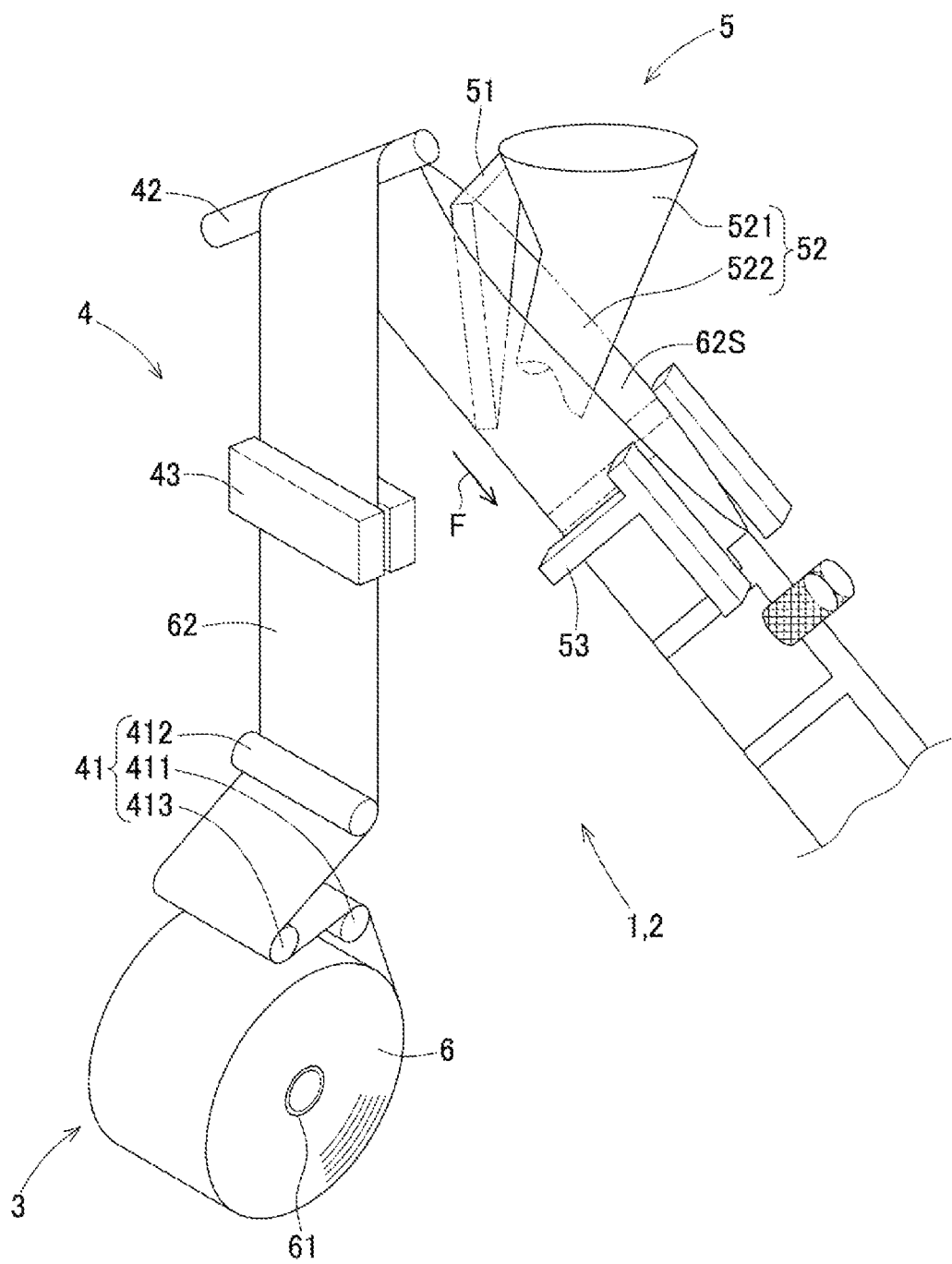
FIG. 1 is a perspective view showing a schematic configuration of a packing section in a medicine packing apparatus according to an embodiment of the present invention.

The present invention will be described by way of one embodiment of a combination of a wound body 6 and a medicine packing apparatus 1. In the following description, a "proximal end side" corresponds to a left side in FIG. 2, and a "distal end side" corresponds to a right side in FIG. 2. Further, in the following description, an "axial direction" is an axial direction of a support shaft 31. Regarding reference numerals allocated to the respective constitutional elements, the same reference numerals are sometimes used for the elements described in different terminologies by taking the functions of those elements into account. The same reference numerals are also allocated for a plurality of constitutional elements having the same shape.

Wound Body

As shown in FIG. 1, the wound body 6 is formed by winding a packing material 62 in a roll shape. The wound body 6 includes a core body 61 and the packing material 62. The core body 61 has a cylindrical shape. Examples of the material of the core body 61 include a hard resin. The packing material 62 has a strip shape. In other words, the packing material 62 has an elongated sheet shape. The packing material 62 includes a base material and a heat welding layer so as to be capable of bonding by heat seal. Examples of the base material include glassine paper and cellophane paper. The heat welding layer is formed on the base material. Examples of the material of the heat welding layer include polyethylene. The packing material 62 is wound around the outer periphery of the core body 62. In this embodiment, the packing material 62 is wound around the outer periphery of the core body 61 while being folded in half along a center in a width direction (short side direction) to have the heat welding layer located inside.

Medicine Packing Apparatus

As shown in FIG. 1, the medicine packing apparatus 1 is configured to pack a medicine using the packing material 62. Examples of the medicine include tablets and powders. The medicine packing apparatus 1 includes the support shaft 31 for supporting the wound body 6. In FIG. 1, the support shaft 31 is omitted. The medicine packing apparatus 1 packs a medicine using the packing material 62 wound off from the wound body 6 supported by the support shaft 31.

The medicine packing apparatus 1 includes a packing section 2 at which the medicine packing is performed. The packing section 2 includes a packing material supply section 3, a packing material conveyance section 4, and a packing body forming section 5. The packing material supply section 3 supplies the packing material 62. The packing material conveyance section 4 conveys the packing material 62 supplied by the packing material supply section 3. The packing body forming section 5 forms a packing body with a medicine packed therein using the packing material 62 conveyed by the packing material conveyance section 4. The packing material 62 is conveyed along its longitudinal direction (direction represented by an arrow F in FIG. 2). The packing material supply section 3, the packing material conveyance section 4, and the packing body forming part 5 are located in this order from the upstream side to the downstream side in the conveyance direction of the packing material 62 in the packing section 2.

Packing Material Supply Section

The packing material supply section 3 is a part for feeding the packing material 62 to the packing material conveyance section 4 and its downstream side. The wound body 6 is arranged in the packing material supply section 3 to be rotatable in the circumferential direction. The packing material 62 is drawn out in the longitudinal direction from the wound body 6 by the rotation of the wound body 6.

Packing Material Conveyance Section

The packing material conveyance section 4 conveys the packing material 62 in the longitudinal direction and supplies the same to the packing body forming part 5 on downstream side. The packing material conveyance section 4 mainly includes a tension adjustment mechanism 41 and a folding bar 42. The tension adjustment mechanism 41 is configured to adjust the tension of the packing material 62 by stretching the packing material 62 among rollers 411 to 413, an inter-axial distance of which is changeable, so as to allow the packing material 62 to be bent backward. The tension adjustment mechanism 41 of this embodiment is formed by the combination of two fixed rollers 411 and 412 with their axial positions immovable and one dancer roller 413 with its axial position movable so as to be curved relative to the mounting base. The folding bar 42 changes the conveyance direction of the packing material 62 conveyed upward from the tension adjustment mechanism 41 to an obliquely downward direction. The packing material conveyance section 4 can include a printing part 43 for printing, for example the medicine prescription information on the surface of the packing material 62.

Packing Body Forming Part

The packing body forming section 5 is a part for supplying each dose of the medicine to the packing material 62 according to the prescription allow it to be packed individually by bonding the packing material 62. The packing body forming section 5 mainly includes a triangular plate 51, a hopper 52, and a packing material bonding part 53. The triangular plate 51 is a part that is located downstream side of the hopper 52 in the conveyance direction and is configured to push open the packing material 62 in a state of being folded in half in the width direction so as to separate one side and the other side of the packing material 62 away from each other to allow the packing material 62 to have a V-shaped cross section as seen in the longitudinal direction. The hopper 52 has an upper part 521 and a lower part 522 that has a horizontally cross sectional area reduced compared with the upper part 521 and that is configured to be partly inserted into a space 62S having the V-shaped cross section which has been push opened by the triangular plate 51 of the packing material 62. The medicine supplied according to the prescription is supplied on the packing material 62 via the inside of the hopper 52 by a medicine supply mechanism (not shown) disposed above the hopper 52. The packing material bonding part 53 is a part configured to, for example, heat melt the packing material 62 to section the packing material 62 into individual packs. The packing body forming section 5 can include another part, for example, a perforation forming part (not shown) configured to form perforations in the packing material 62 bonded by the packing material bonding part 53 for ease of cutting.

Support Shaft

Figure 2:
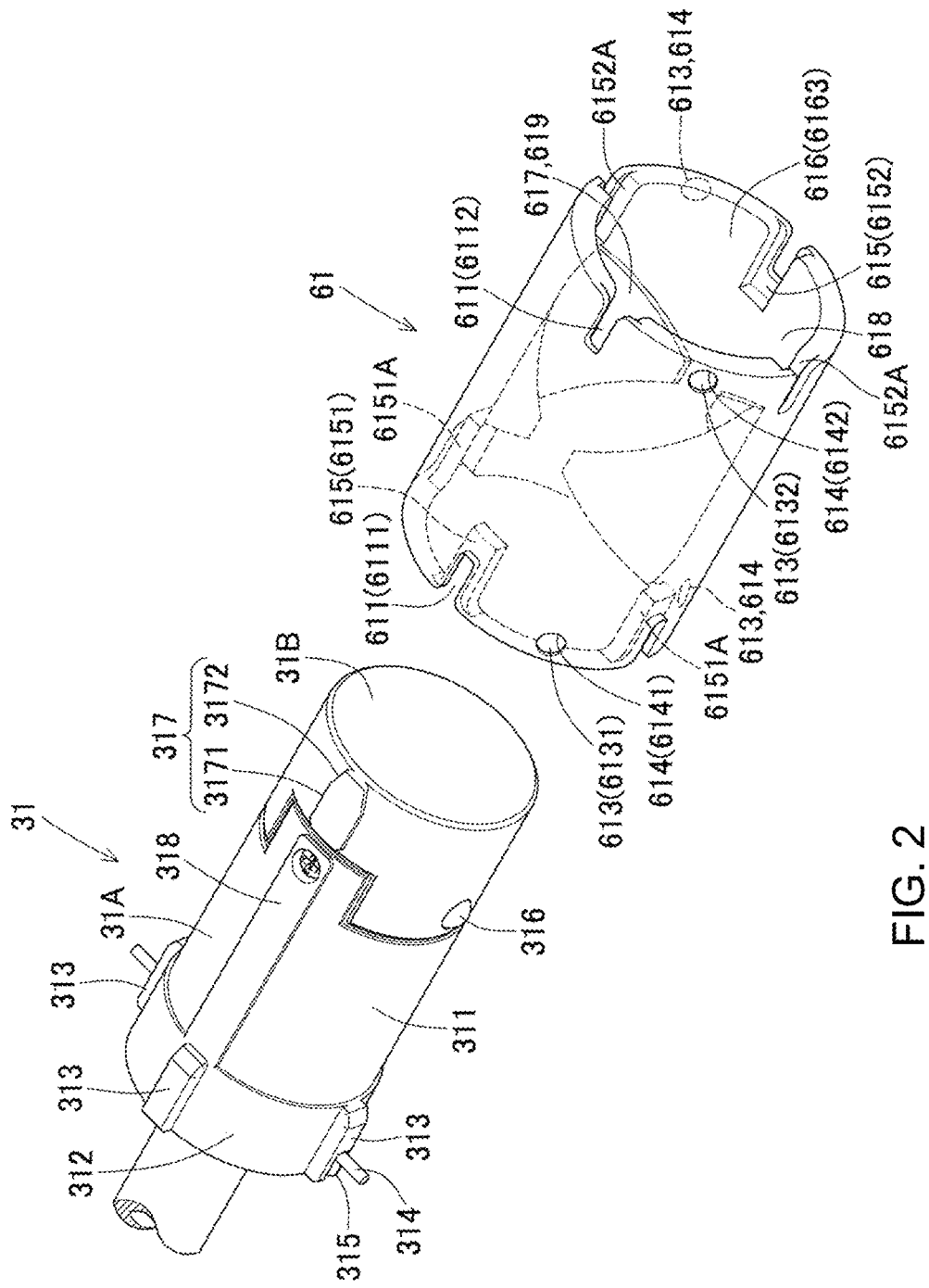
FIG. 2 is a perspective view showing a support shaft and a core body of a wound body in the packing section.

As shown in FIG. 2, the support shaft 31 has a columnar shape. The support shaft 31 has, as its part, an outer peripheral part having a cylindrical shape. The wound body 6, more specifically, the core body 61 of the wound body 6 is mounted on an outer periphery of the outer peripheral part of the support shaft 31 (i.e., outer periphery of the support shaft 31).

The support shaft 31 is rotatably mounted to the mounting base. In FIG. 2, the mounting base is not illustrated while being actually located on the left side. The support shaft 31 is rotatable around a central axis of the outer peripheral part of the support shaft 31 (i.e., central axis of the support shaft 31).

The support shaft 31 is driven by a driving unit. The driving unit is disposed inside the mounting base. Examples of the driving unit include a stepping motor. The driving unit rotates the support shaft 31 in a first rotation direction and a second rotation direction opposite to the first rotation direction. Rotation of the support shaft 31 in the first direction allows the packing material 62 to be wound off from the wound body 6 supported by the support shaft 31. Rotation of the support shaft 31 in the second rotation direction allows the packing material 62 to be wound back on the wound body 6. The driving unit intermittently rotates the support shaft 31 according to the conveyance of the packing material 62 to the packing body forming section 5.

The support shaft 31 is cantilever-supported relative to the mounting base. The support shaft 31 has a proximal end (left part in FIG. 2) and a distal end (right part in FIG. 2). The core body 61 is mounted on the outer periphery of the support shaft 31 from the distal end side of the support shaft 31. A direction from the distal end of the support shaft 31 toward the proximal end of the support shaft 31 will be hereinafter sometimes referred to as the "mounting direction", and a direction from the proximal end of the support shaft 31 toward the distal end of the support shaft 31 will be hereinafter sometimes referred to as the "dismounting direction".

The support shaft 31 includes a support shaft main body 31A and a support shaft distal end body 31B. The support shaft main body 31A is a part including the proximal end of the support shaft 31. The support shaft distal end body 31B is a part including the distal end of the support shaft 31. The support shaft distal end body 31B is provided separately from the support shaft main body 31A and is mounted to the distal end of the support shaft main body 31A. The inside of the support shaft main body 31A is exposed to the outside by dismounting the support shaft distal end body 31B from the support shaft main body 31A. Because of this, when a later-described magnetic detecting part or the like is mounted inside the support shaft 31, a mounting operation and a maintenance operation for such a part can be facilitated. The support shaft distal end body 31B can be formed integrally with the support shaft main body 31A. The support shaft distal end body 31B functions as a mount-assisting part for assisting the operation for mounting the core body 61 to the support shaft main body 31A. The support shaft distal end body 31B is used in combination with the wound body 6 of this embodiment.

As an alternative configuration based on a different perspective from the aforementioned support shaft main body 31A and support shaft distal end body 31B, it can be said that the support shaft 31 includes a main shaft part 311 and a proximal end shaft part 312. The main shaft part 311 is a part including the distal end of the support shaft 31. The main shaft part 311 has a constant radial dimension. The proximal end shaft part 312 is located closer to the proximal end of the support shaft 31 than the main shaft part 311. The proximal end shaft part 312 is a part including the proximal end of the support shaft 31. The proximal end shaft part 312 has a larger radial dimension than the main shaft part 311. As shown in FIG. 2, a step extending in the circumferential direction is formed between the main shaft part 311 and the proximal end shaft part 312.

The outer peripheral part of the support shaft 31 has at least one first projection 313 (a plurality of projections, specifically four projections in this embodiment), at least one second projection 317 (a plurality of projections, specifically two projections in this embodiment), and at least one third projection 318 (one projection in this embodiment).

The first projections 313 are located at the proximal end of the support shaft 31 and project outward in the radial direction of the support shaft 31. The first projections 313 are disposed on the support shaft main body 31A. The first projections 313 are disposed on the proximal end shaft part 312. The first projections 313 located at the proximal end of the support shaft 31 extend in the axial direction of the support shaft 31.

The first projections 313 are arranged with a certain angular distance from each other in the circumferential direction of the support shaft 31. The first projections 313 are arranged with equal angular distance from each other in the circumferential direction of the support shaft 31. In this embodiment, four first projections 313 are arranged at intervals of 90° in the circumferential direction of the support shaft 31. When the support shaft 31 is seen from the proximal end side and the angular position of a first one of the first projections 313 located on the top in FIG. 2 is designated as an angle of 0° as a reference position in the circumferential direction of the support shaft 31 (this position is also referred as a reference for the angular position regarding the support shaft 31 in the following description), a second one of the first projections 313 (as shown on the front side in FIG. 2) is located at an angle of 90°, a third one of the first projections 313 (not shown in FIG. 2 because it is located opposite to the first one of the first projections 313 in the radial direction) is located at an angle of 180°, and a fourth one of the first projections 313 (as shown on the back side in FIG. 2) is located at an angle of 270° respectively in the clockwise direction.

The second projections 317 are located at the distal end of the support shaft 31 and project outward in the radial direction of the support shaft 31. The second projections 317 are disposed on the support shaft distal end body 31B. The second projections 317 are disposed on the main shaft part 311. The second projections 317 located at the distal end of the support shaft 31 extend in the axial direction of the support shaft 31. A projecting amount of the second projections 317 projecting outward in the radial direction with respect to the outer peripheral part of the support shaft 31 is smaller than that of the first projections 313.

Each of the second projections 317 has a main body part 3171 and a tapered part 3172. The main body part 3171 has a constant width (dimension in the circumferential direction of the support shaft 31) in the axial direction of the support shaft 31. The tapered part 3172 is disposed on the distal end side of the support shaft 31 relative to the main body part 3171. The tapered part 3172 is continuous with the main body part 3171. The tapered part 3172 has opposite sides in the width direction (circumferential direction of the support shaft 31) gradually coming closer to each other as they advance from the proximal end of the support shaft 31 toward the distal end of the support shaft 31.

The second projections 317 are arranged with a certain angular distance from each other in the circumferential direction of the support shaft 31. The second projections 317 are arranged with equal angular distance from each other in the circumferential direction of the support shaft 31. In this embodiment, two second projections 317 are arranged at intervals of 180°. Further, in this embodiment, the two second projections 317 are respectively located at the same angular positions as those of two of the four first projections 313 in the circumferential direction of the support shaft 31. When the support shaft 31 is seen from the proximal end side and the angular position of the first one of the first projections 313 is designated as an angle of 0° in the circumferential direction of the support shaft 31, first and second ones of the second projections 317 are located respectively at angles of 0° and 180°.

The third projection 318 is disposed at an intermediate position between the proximal end of the support shaft 31 and the distal end of the support shaft 31, and projects outward in the radial direction of the support shaft 31. The third projection 318 is disposed on the support shaft main body 31A. The third projection 318 is disposed on the main shaft part 311. The third projection 318 extends in the axial direction of the support shaft 31 in the intermediate part between the proximal end of the support shaft 31 and the distal end of the support shaft 31. A projecting amount of the third projection 318 projecting outward in the radial direction with respect to the outer peripheral part of the support shaft 31 is smaller than that of the first projections 313. The projecting amount of the third projection 318 projecting outward in the radial direction with respect to the outer peripheral part of the support shaft 31 is equal to that of the second projections 317. The third projection 318 has a width (dimension in the circumferential direction of the support shaft 31) is constant in the axial direction of the support shaft 31. The width of the third projection 318 is equal to the width of the main body part 3171 of each of the second projections 317.

The third projection 318 is located at a certain angular position in the circumferential direction of the support shaft 31. In this embodiment, the third projection 318 is located at the same angular position as that of one of the two second projections 317. When the support shaft 31 is seen from the proximal end side and the angular position of the first one of the first projections 313 is designated as an angle of 0°, the third projection 318 is located at an angle of 0°.

The support shaft 31 includes at least one retractable part 316 (a plurality of retractable parts, specifically two retractable parts in this embodiment). The retractable parts 316 are located close to the distal end of the support shaft 31. The retractable parts 316 are disposed in the support shaft distal end body 31B. The retractable parts 316 can be disposed in the support shaft main body 31A. The retractable parts 316 are disposed in the main shaft part 311.

The retractable parts 316 are configured to be retractable and extendable relative to the outer peripheral part of the support shaft 31. The retractable parts 316 have a spherical or hemispherical shape. The retractable parts 316 are positioned inside the support shaft 31. The outer peripheral part of the support shaft 31 has the same number of circular holes as the number of the retractable parts 316. The circular holes extend through the outer peripheral part of the support shaft 31 in the radial direction of the support shaft 31. The retractable parts 316 are configured to partly project outward in the radial direction from the circular holes. Each of the retractable parts 316 is biased outward in the radial direction of the support shaft 31 by a spring not shown in Figures. The spring is disposed inside the support shaft 31.

The retractable parts 316 are arranged with a certain angular distance from each other in the circumferential direction of the support shaft 31. The retractable parts 316 are arranged with equal angular distance from each other in the circumferential direction of the support shaft 31. In this embodiment, two retractable parts 316 are arranged at intervals of 180° in the circumferential direction of the support shaft 31. Further, in this embodiment, the two retractable parts 316 are respectively located at the different angular positions from those of the two second projections 317. Specifically, the two retractable parts 316 are located at angular positions 90° different respectively from the two second projections 317 in the circumferential direction of the support shaft 31. The two retractable parts 316 are located at the same angular positions as those of the second one and the fourth one of the first projections 313 in the circumferential direction of the support shaft 31. When the support shaft 31 is seen from the proximal end side and the angular position of the first one of the first projections 313 is designated as an angle of 0° in the circumferential direction of the support shaft 31, the first one and the second one of the retractable parts 316 are located at angles of 90° and 270° respectively in the clockwise direction.

The support shaft 31 further includes at least one movable part 314 (a plurality of movable parts, specifically two movable parts in this embodiment). The movable parts 314 are located at the proximal end of the support shaft 31. The movable parts 314 are disposed in the support shaft main body 31A. The movable parts 314 are disposed in the proximal end shaft part 312. The movable parts 314 are movable in the axial direction of the support shaft 31. The movable parts 314 have a rod shape and extend in the radial direction of the support shaft 31. Each of the movable parts 314 has a leading end that projects outward in the radial direction of the support shaft 31 from the outer peripheral surface of the core body 61 in a state where the core body 61 is mounted on the outer periphery of the support shaft 31. The movable parts 314 are movable between a retracted position and an advanced position. The advanced position is a position at which each of the movable parts 314 which has advanced from the retracted position in a direction from the proximal end of the support shaft 31 toward the distal end of the support shaft 31 is located. Each of the movable parts 314 is biased in a direction from the proximal end of the support shaft 31 toward the distal end of the support shaft 31 by a spring not shown in Figures. The spring is disposed inside the support shaft 31.

The movable parts 314 are arranged with a certain angular distance from each other in the circumferential direction of the support shaft 31. The movable parts 314 are arranged with equal angular distance from each other in the circumferential direction of the support shaft 31. In this embodiment, two movable parts 314 respectively as first and second movable parts 314 are arranged at intervals of 180° in the circumferential direction of the support shaft 31. Further, in this embodiment, the two movable parts 314 are respectively located at the same angular positions of the second one and the fourth one of the first projections 313 in the circumferential direction of the support shaft 31. Therefore, the two movable parts 314 project outward in the radial direction from the second one and the fourth one of the first projections 313. When the support shaft 31 is seen from the proximal end side and the angular position of the first one of the first projections 313 is designated as an angle of 0° in the circumferential direction of the support shaft 31, the first and second movable parts 314 are located respectively at angles of 90° and 270°.

The first movable part 314 is located at the second one of the first projections 313 that is located at an angle of 90° relative to the first one of the first projections 313 (angular position of 0°). A first long hole 315 which acts as a cutout extending in the axial direction of the support shaft 31 is formed in a radial outer surface of the second one of the first projections 313. The first long hole 315 extends through the second one of the first projections 313 in the radial direction of the support shaft 31. The first movable part 314 extends through the first long hole 315 to allow a part of it including its leading end to project outward from the first long hole 315 in the radial direction of the support shaft 31.

On the other hand, the second movable part 314 is disposed at the fourth one of the first projections 313 that is located at an angle of 270° relative to the first one of the first projections 313 (angular position of 0°). A second long hole 315 (not shown) which acts as a cutout extending in the axial direction of the support shaft 31 is formed in a radial outer surface of the fourth one of the first projections 313. The second long hole 315 extends through the fourth one of the first projections 313 in the radial direction of the support shaft 31. The second movable part 314 extends through the second long hole 315 to allow a part of it including its leading end to project outward from the second long hole 315 in the radial direction of the support shaft 31.

Core Body

Figure 3:
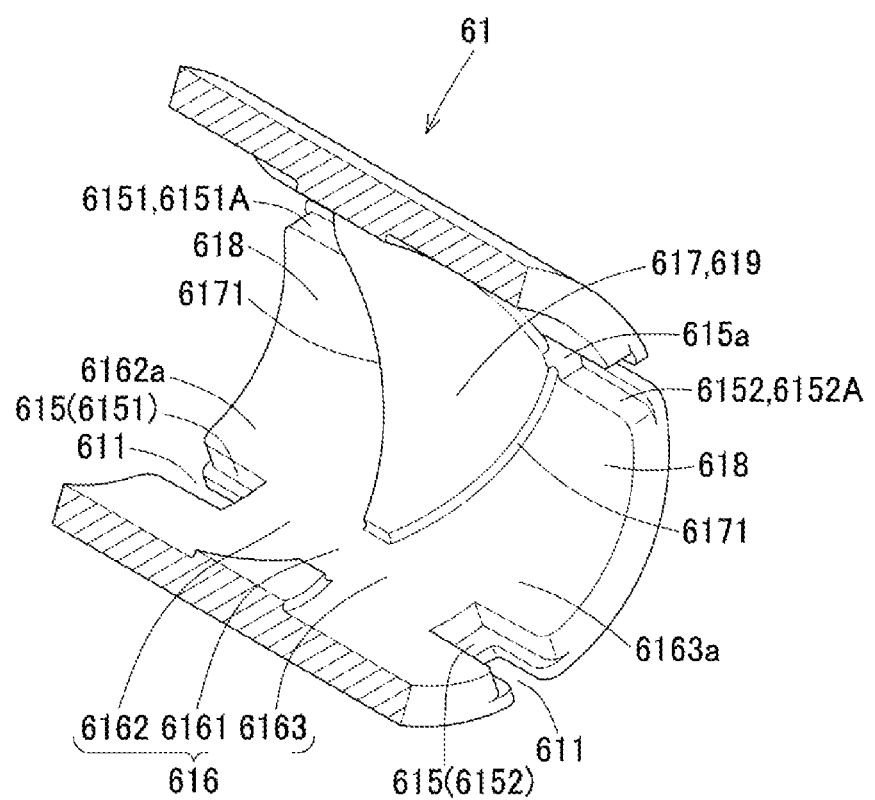
FIG. 3 is a cross sectional perspective view along an axis of the core body showing a half of the core body.

As shown in FIG. 2 and FIG. 3, the core body 61 has a cylindrical shape. The core body 61 has, as its parts, an outer peripheral part having a cylindrical shape that is an outside area in the radial direction, and an inner peripheral part (not shown) having a cylindrical shape that is an inside area in the radial direction. The core body 61 has one end (left end in FIG. 2 and FIG. 3) and an other end (right end in FIG. 2 and FIG. 3). The core body 61 is formed basically symmetrically based on a virtual plane that is positioned at the center in an axial direction parallel to a central axis of the core body 61 and that is orthogonal to the central axis. That is, the shape of the core body 61 on the one end side and the shape of the core body 61 on the other end side have a mirror image relationship. The thus configured core body 61 can be mounted on the outer periphery of the support shaft 31 from any of the one end side and the other end side of the core body 61.

The core body 61 has an outer diameter constant in the axial direction of the core body 61. No step is formed on the outer periphery of the outer peripheral part of the core body 61. Therefore, the packing material 62 which has been wound around the outer periphery of the core body 61 is prevented from generating level difference marks.

Formed in the inner peripheral part of the core body 61 are at least one one-end-side first recess part 6151 (a plurality of recesses, specifically four recesses in this embodiment), at least one other-end-side first recess part 6152 (a plurality of recesses, specifically four recesses in this embodiment), and at least one second recess part 616 (a plurality of recesses, specifically two recesses in this embodiment). The one-end-side first recess parts 6151 and the other-end-side first recess parts 6152 function as first recess parts 615.

The number of the one-end-side first recess parts 6151 is equal to the number of the first projections 313 of the support shaft 31. The number of the one-end-side first recess parts 6151 can be larger than the number of the first projections 313 of the support shaft 31. The number of the other-end-side catch recess parts 6152 is equal to the number of the first projections 313 of the support shaft 31. The number of the other-end-side catch recess parts 6152 can be larger than the number of the first projections 313 of the support shaft 31. The number of the second recess parts 616 is equal to the number of the second projections 317 of the support shaft 31. The number of the second recess parts 616 can be larger than the number of the second projections 317 of the support shaft 31.

The one-end-side first recess parts 6151 respectively engage the first projections 313 of the support shaft 31 when the core body 61 has been mounted on the outer periphery of the support shaft 31 from the one end side of the core body 61. The one-end-side first recess parts 6151 are located at the one end of the core body 61 and recess outward in the radial direction of the core body 61.

The one-end-side first recess parts 6151 are arranged with a certain angular distance from each other in the circumferential direction of the core body 61. The one-end-side first recess parts 6151 are arranged with equal angular distance from each other in the circumferential direction of the core body 61. In this embodiment, four one-end-side first recess parts 6151 are arranged at intervals of 90° in the circumferential direction of the core body 61. When the core body 61 is seen from the one end side and the angular position of a first one of the one-end-side first recess parts 6151 is designated as an angle of 0° as a reference position in the circumferential direction of the core body 61 (this position is also referred as a reference for the angular position regarding the core body 61 in the following description), second to fourth ones of the one-end-side first recess parts 6151 are located at angles of 90°, 180°, and 270° respectively in the clockwise direction. The relationship of these angular positions is the same as the relationship of the angular positions of the four first projections 313 of the support shaft 31.

The one-end-side first recess parts 6151 are located at the one end of the core body 61 and extend in the axial direction of the core body 61. Each of the one-end-side first recess parts 6151 has an end that is located at the one end of the core body 61, more specifically at a position displaced from an end face of the one end of the core body 61 (hereinafter referred to as "one end face") toward the other end of the core body 61. The one-end-side first recess parts 6151 extend to the one end face of the core body 61 and open at the one end face of the core body 61. Each of the one-end-side first recess parts 6151 expands toward both sides in the circumferential direction of the core body 61 as it advances toward the one end face of the core body 61 in the proximity of the one end face of the core body 61.

The other-end-side first recess parts 6152 engage the first projections 313 of the support shaft 31 when the core body 61 has been mounted on the outer periphery of the support shaft 31 from the other end side of the core body 61. The other-end-side first recess parts 6152 are located at the other end of the core body 61 and recess outward in the radial direction of the core body 61.

The other-end-side first recess parts 6152 are arranged with a certain angular distance from each other in the circumferential direction of the core body 61. The other-end-side first recess parts 6152 are arranged with equal angular distance from each other in the circumferential direction of the core body 61. In this embodiment, four other-end-side first recess parts 6152 are arranged at intervals of 90° in the circumferential direction of the core body 61. Further, in this embodiment, the four other-end-side first recess parts 6152 are respectively located at the same angular positions as those of the four one-end-side first recess parts 6151 in the circumferential direction of the core body 61. When the core body 61 is seen from the one end side and the angular position of the first one of the one-end-side first recess parts 6151 is designated as an angle of 0° in the circumferential direction of the core body 61, first to fourth ones of the other-end-side first recess parts 6152 are located respectively at angles of 0°, 90°, 180°, and 270° respectively in the clockwise direction. The relationship of these angular positions is the same as the relationship of the angular positions of the four first projections 313 of the support shaft 31 in the same manner as the one-end-side first recess parts 6151.

The other-end-side first recess parts 6152 are located at the other end of the core body 61 and extend in the axial direction of the core body 61. Each of the other-end-side first recess parts 6152 has an end that is located at the other end of the core body 61, more specifically at a position displaced from an end face of the other end of the core body 61 (hereinafter referred to as "other end face") toward the one end of the core body 61. The other-end-side first recess parts 6152 extend to the other end face of the core body 61 and open at the other end face of the core body 61. Each of the other-end-side first recess parts 6152 expands toward both sides in the circumferential direction of the core body 61 as it advances toward the other end face of the core body 61 in the proximity of the other end face of the core body 61.

The second recess parts 616 engage the second projections 317 of the support shaft 31 when the core body 61 is mounted on the outer periphery of the support shaft 31. The second recess parts 616 are located to extend from the one end of the core body 61 to the other end of the core body 61 and recess outward in the radial direction of the core body 61. The recessing amount of the second recess parts 616 recessing outward in the radial direction of the core body 61 with respect to the inner peripheral part (specifically, the inner peripheral surface of the core body 61) is smaller than that of the one-end-side first recess parts 6151 and the other-end-side first recess parts 6152. Thus, it is possible to prevent lowering of the strength of the core body 61 due to the formation of the second recess parts 616.

The second recess parts 616 are arranged with a certain angular distance from each other in the circumferential direction of the core body 61. The second recess parts 616 are arranged with equal angular distance from each other in the circumferential direction of the core body 61. In this embodiment, two second recess parts 616 are arranged at intervals of 180° in the circumferential direction of the core body 61. Further, in this embodiment, the two second recess parts 616 are respectively located at the same angular positions as those of two of the four one-end-side first recess parts 6151 in the circumferential direction of the core body 61. When the core body 61 is seen from the one end side and the angular position of the first one of the one-end-side first recess parts 6151 is designated as an angle of 0° in the circumferential direction of the core body 61, first to second ones of the second recess parts 616 are located respectively at angles of 0° and 180°. The relationship of these angular positions is the same as the relationship of the angular positions of the two second projections 317 of the support shaft 31.

The second recess parts 616 extend between the one end of the core body 61 and the other end of the core body 61 in the axial direction. The second recess parts 616 extend to the one end face of the core body 61 and open at the one end face of the core body 61. The second recess parts 616 are continuous with each other in the circumferential direction of the core body 61 at the one end of the core body 61. That is, the second recess parts 616 are formed along the entire circumference of the core body 61 at the one end of the core body 61. The second recess parts 616 extend to the other end face of the core body 61 and open at the other end face of the core body 61. The second recess parts 616 are continuous with each other in the circumferential direction of the core body 61. That is, the second recess parts 616 are formed along the entire circumference of the core body 61 at the other end of the core body 61.

As shown in FIG. 3, each of the second recess parts 616 includes an one-end-side leading part 6162, an other-end-side leading part 6163, and a guide part 6161.

The one-end-side leading part 6162 is configured to lead the second projection 317 when the core body 61 is mounted on the outer periphery of the support shaft 31 from the one end side of the core body 61. The one-end-side leading part 6162 is located close to the one end of the core body 61. The one-end-side leading part 6162 is located closer to the one end of the core body 61 than the width center of the core body 61. The one-end-side leading part 6162 has a width parallel to the circumferential direction of the core body 61, which gradually reduces as it advances from the one end of the core body 61 toward the other end of the core body 61. The one-end-side leading part 6162 has opposite sides in the circumferential direction of the core body 61, which come closer to each other as they advance from the one end of the core body 61 toward the other end of the core body 61.

The other-end-side leading part 6163 is configured to lead the second projection 317 when the core body 61 is mounted on the outer periphery of the support shaft 31 from the other end side of the core body 61. The other-end-side leading part 6163 is located close to the other end of the core body 61. The other-end-side leading part 6163 is located closer to the other end of the core body 61 than the width center of the core body 61. The other-end-side leading part 6163 has a width parallel to the circumferential direction of the core body 61, which gradually reduces as it advances from the other end of the core body 61 toward the one end of the core body 61. The other-end-side leading part 6163 has opposite sides in the circumferential direction of the core body 61, which come closer to each other as they advance from the other end of the core body 61 toward the one end of the core body 61.

The guide part 6161 is configured to guide the second projection 317 when the core body 61 is mounted on the outer periphery of the support shaft 31. The guide part 6161 is located between the one-end-side leading part 6162 and the other-end-side leading part 6163. In this embodiment, the guide part 6161 is located at the width center of the core body 61. The guide part 6161 is located closer to the other end of the core body 61 than the one-end-side leading part 6162. The guide part 6161 is continuous with the one-end-side leading part 6162. The guide part 6161 is located closer to the one side of the core body 61 than the other-end-side leading part 6163. The guide part 6161 is continuous with the other-end-side leading part 6163.

The guide part 6161 has a constant width (dimension in the circumferential direction of the core body 61) in the axial direction of the core body 61. The width of the guide part 6161 is substantially equal to the width of the second projections 317 of the support shaft 31 (dimension in the circumferential direction of the support shaft 31), specifically to the width of the main body part 3171 of the second projections 317. The width of the guide part 6161 is slightly larger than the width of the second projection 317 to the extent which allows the second projection 317 to move through the guide part 6161 in the axial direction of the core body 61.

It can be said that each of the second recess parts 616 has a free area, a transition area, and a limitation area. In each of the second recess parts 616, an area corresponding in position the one end of the core body 61 and an area corresponding in position the other end of the core body 61 are free areas. The free areas permit rotation of the core body 61 relative to the support shaft 31 without limitation. The areas of the one-end-side leading part 6162 and the other-end-side leading part 6163 are transition areas. Each of the transition areas is configured such that the range within which the core body 61 is rotatable becomes small toward the center in the axial direction of the core body 61. The area of the guide part 6161 is a limitation area. In the limitation area, limitation is applied so that the core body 61 cannot substantially rotate.

The inner peripheral part of the core body 61 includes at least one inner peripheral surface part 617 (a plurality of parts, specifically two parts in this embodiment). Each of the inner peripheral surface parts 617 forms an inner peripheral surface of the core body 61. Each of the inner peripheral surface parts 617 is located between the one end of the core body 61 and the other end of the core body 61. Each of the inner peripheral surface parts 617 is located to be surrounded by the second recess part 616 in the circumferential direction.

The inner peripheral surface parts 617 are arranged with a certain angular distance from each other in the circumferential direction of the core body 61. The inner peripheral surface parts 617 are arranged with equal angular distance from each other in the circumferential direction of the core body 61. In this embodiment, two inner peripheral surface parts 617 are arranged at intervals of 180° in the circumferential direction of the core body 61. Further, in this embodiment, the two inner peripheral surface parts 617 are located at angular positions displaced 90° from the corresponding two second recess parts 616 in the circumferential direction of the core body 61. When the core body 61 is seen from the one end side of the core body 61 and the angular position of a first one of the one-end-side first recess parts 6151 is designated as an angle of 0° in the circumferential direction of the core body 61, the first and second ones of the inner peripheral surface parts 617 are located at angles of 90° and 270° respectively in the clockwise direction.

Each of the inner peripheral surface parts 617 is located at a middle position between the one end of the core body 61 and the other end of the core body 61 and extends in the axial direction. However, each of the inner peripheral surface parts 617 does not reach the one end face of the core body 61. The one end of the first one of the inner peripheral surface parts 617 is continuous with the end of the second one of the one-end-side first recess parts 6151. The one end of the second one of the inner peripheral surface parts 617 is continuous with the end of the fourth one of the one-end-side first recess parts 6151. Each of the inner peripheral surface parts 617 does not reach the other end face of the core body 61. The other end of the first one of the inner peripheral surface parts 617 is continuous with the end of the second one of the other-end-side first recess parts 6152. The other end of the second one of the inner peripheral surface parts 617 is continuous with the end of the fourth one of the other-end-side first recess parts 6152.

The inner peripheral surface parts 617 have a shape corresponding to the shape of the second recess parts 616. A part of each of the inner peripheral surface parts 617 which is close to the one end expands toward both sides in the circumferential direction of the core body 61 as it advances from the one end of the core body 61 toward the other end of the core body 61 so as to correspond to the shape of each of the one-end-side leading parts 6162. A part of each of the inner peripheral surface parts 617 which is close to the other end expands toward both sides in the circumferential direction of the core body 61 as it advances from the other end of the core body 61 toward the one end of the core body 61. The center part in the axial direction of each of the inner peripheral surface parts 617 has a width (dimension in the circumferential direction of the core body 61) constant in the axial direction of the core body 61.

It can be said that the core body 61 has small thickness parts 618 and large thickness parts 619. The small thickness parts 618 correspond to the second recess parts 616. The large thickness parts 619 have a thickness larger than the small thickness parts 618. The large thickness parts 619 correspond to the inner peripheral surface parts 617.

The inner peripheral part of the core body 61 further has at least one first catch recess part 6152A (a plurality of recesses, specifically two recesses in this embodiment), and at least one second catch recess part 6151A (a plurality of recesses, specifically two recesses in this embodiment).

The retractable parts 316 are caught by the first catch recess parts 6152A when the core body 61 has been mounted on the outer periphery of the support shaft 31 from the one end side of the core body 61. The first catch recess parts 6152A are located close to the other end of the core body 61 and recess outward in the radial direction of the core body 61. Each of the first catch recess parts 6152A has a step part 615a facing the other end side of the core body 61.

The first catch recess parts 6152A are arranged with a certain angular distance from each other in the circumferential direction of the core body 61. The first catch recess parts 6152A are arranged with equal angular distance from each other in the circumferential direction of the core body 61. In this embodiment, two first catch recess parts 6152A are arranged at intervals of 180° in the circumferential direction of the core body 61. Further, in this embodiment, the two first catch recess parts 6152A are located, as first and second ones of the first catch recess parts 6152A, respectively at the same angular positions as those of the two inner peripheral surface parts 617. When the core body 61 is seen from the one end side of the core body 61 and the angular position of the first one of the one-end-side first recess parts 6151 is designated as an angle of 0° in the circumferential direction of the core body 61, the first and second first catch recess parts 6152A are located at angles of 90° and 270° respectively in the clockwise direction.

The first one of the first catch recess parts 6152A is formed integrally with the second one of the other-end-side first recess parts 6152. That is, these recesses are formed as an integrated recess in this embodiment. The first one of the first catch recess parts 6152A can be formed separately from the second one of the other-end-side first recess parts 6152. For example, the first one of the first catch recess parts 6152A can be located closer to the center part in the axial direction of the core body 61 than the second one of the other-end-side first recess parts 6152.

The second one of the first catch recess parts 6152A is formed integrally with the fourth one of the other-end-side first recess parts 6152. That is, these recesses are formed as an integrated recess in this embodiment. The second one of the first catch recess parts 6152A can be formed separately from the fourth one of the other-end-side first recess parts 6152. For example, the second one of the first catch recess parts 6152A can be located closer to the center part in the axial direction of the core body 61 than the fourth one of the other-end-side first recess parts 6152.

The retractable parts 316 are caught by the second catch recess parts 6151A when the core body 61 has been mounted on the outer periphery of the support shaft 31 from the other end side of the core body 61. The second catch recess parts 6151A are located close to the one end of the core body 61 and recess outward in the radial direction of the core body 61. Each of the second catch recess parts 6151A has a step part 615*a* facing the one end side of the core body 61.

The second catch recess parts 6151A are arranged with a certain angular distance from each other in the circumferential direction of the core body 61. The second catch recess parts 6151A are arranged with equal angular distance from each other in the circumferential direction of the core body 61. In this embodiment, two second catch recess parts 6151A are arranged at intervals of 180° in the circumferential direction of the core body 61. Further, in this embodiment, the two second catch recess parts 6151A are located, as first and second ones of the second catch recess parts 6151A, respectively at the same angular positions as those of the two inner peripheral surface parts 617. When the core body 61 is seen from the one end side of the core body 61 and the angular position of the first one of the one-end-side first recess parts 6151 is designated as an angle of 0° in the circumferential direction of the core body 61, the first and second ones of the second catch recess parts 6151A are located at angles of 90° and 270° respectively in the clockwise direction.

The first one of the second catch recess parts 6151A is formed integrally with the second one of the one-end-side first recess parts 6151. That is, these recesses are formed as an integrated recess in this embodiment. The first one of the second catch recess parts 6151A can be formed separately from the second one of the one-end-side first recess parts 6151. For example, the first one of the second catch recess parts 6151A can be located closer to the center part in the axial direction of the core body 61 than the second one of the one-end-side first recess parts 6151.

The second one of the second catch recess parts 6151A is formed integrally with the fourth one of the one-end-side first recess parts 6151. That is, these recesses are formed as an integrated recess in this embodiment. The second one of the second catch recess parts 6151A can be formed separately from the fourth one of the one-end-side first recess parts 6151. For example, the second one of the second catch recess parts 6151A can be located closer to the center part in the axial direction of the core body 61 than the fourth one of the one-end-side first recess parts 6151.

The core body 61 has at least one one-end-side cutout 6111 (a plurality of cutouts, specifically four cutouts in this embodiment) and at least one other-end-side cutout 6112 (a plurality of cutouts, specifically four cutouts in this embodiment). The one-end-side cutouts 6111 and the other-end-side cutouts 6112 function as cutouts 611.

The movable parts 314 can enter the one-end-side cutouts 6111 from the one end side of the core body 61. The one-end-side cutouts 6111 are located at the one end of the core body 61, and cut out from the one end face of the core body 61 toward the other end of the core body 61. The one-end-side cutouts 6111 extend through the core body 61 in the radial direction of the core body 61. The one-end-side cutouts 6111 are located at the one end of the core body 61 and extend in the axial direction of the core body 61.

The one-end-side cutouts 6111 are arranged with a certain angular distance from each other in the circumferential direction of the core body 61. The one-end-side cutouts 6111 are arranged with equal angular distance from each other in the circumferential direction of the core body 61. In this embodiment, four one-end-side cutouts 6111 are arranged at intervals of 90° in the circumferential direction of the core body 61. Further, in this embodiment, the four one-end-side cutouts 6111 are located respectively at the same angular positions as those of the four one-end-side first recess parts 6151 in the circumferential direction of the core body 61. When the core body 61 is seen from the one end side of the core body 61 and the angular position of the first one of the one-end-side first recess parts 6151 is designated as an angle of 0° in the circumferential direction of the core body 61, the first to fourth ones of the one-end-side cutouts 6111 are located at angles of 0°, 90°, 180°, and 270° respectively in the clockwise direction. The relationship of these angular positions is the same as the relationship of the angular positions of the four first projections 313 of the support shaft 31. The first and third ones of the one-end-side cutouts 6111 may be eliminated as long as the second and fourth ones of the one-end-side cutouts 6111 are provided.

The movable parts 314 can enter the other-end-side cutouts 6112 from the other end side of the core body 61. The other-end-side cutouts 6112 are located at the other end of the core body 61, and cut out from the other end face of the core body 61 toward the one end of the core body 61. The other-end-side cutouts 6112 extend through the core body 61 in the radial direction of the core body 61. The other-end-side cutouts 6112 are located at the other end of the core body 61 and extend in the axial direction of the core body 61.

The other-end-side cutouts 6112 are arranged with a certain angular distance from each other in the circumferential direction of the core body 61. The other-end-side cutouts 6112 are arranged with equal distance from each other in the circumferential direction of the core body 61. In this embodiment, four other-end-side cutouts 6112 are arranged at intervals of 90° in the circumferential direction of the core body 61. Further, in this embodiment, the four other-end-side cutouts 6112 are respectively located at the same angular positions as those of the four other-end-side first recess parts 6152 in the circumferential direction of the core body 61. When the core body 61 is seen from the one end side of the core body 61 and the angular position of the first one of the one-end-side first recess parts 6151 is designated as an angle of 0° in the circumferential direction of the core body 61, the first to fourth ones of the other-end-side cutouts 6112 are located at angles of 0°, 90°, 180°, and 270° respectively in the clockwise direction. The relationship of these angular positions is the same as the relationship of the angular positions of the four first projections 313 of the support shaft 31. The first and third ones of the other-end-side cutouts 6112 may be eliminated as long as the second and fourth ones of the other-end-side cutouts 6112 are provided.

The core body 61 includes at least one one-end-side magnet 6131 (a plurality of magnets, specifically two magnets in this embodiment), and at least one other-end-side magnet 6132 (a plurality of magnets, specifically two magnets in this embodiment). The one-end-side magnets 6131 and the other-end-side magnets 6132 function as magnets 613.

The one-end-side magnets 6131 are located at the one end of the core body 61. The one-end-side magnets 6131 are located according to a first positional relationship in the circumferential direction of the core body 61. The one-end-side magnets 6131 are located with a certain angular distance from each other in the circumferential direction of the core body 61. In this embodiment, two one-end-side magnets 6131 are arranged at intervals of 90° in the circumferential direction of the core body 61. Further, in this embodiment, the two one-end-side magnets 6131 are located respectively at angular positions different from those of the four one-end-side first recess parts 6151 in the circumferential direction of the core body 61. When the core body 61 is seen from the one end side of the core body 61 and the angular position of the first one of the one-end-side first recess parts 6151 is designated as an angle of 0° in the circumferential direction of the core body 61, first and second ones of the one-end-side magnets 6131 are located at angles of 45° and 135° respectively in the clockwise direction.

One-end-side retention parts 6141 are formed at the one end of the core body 61 in the same number as the one-end-side magnets 6131. The One-end-side retention parts 6141 function as magnet retention parts 614 for retaining the magnets 613. The one-end-side retention parts 6141 respectively retain the one-end-side magnets 6131. The one-end-side retaining parts 6141 recess inward from the outer peripheral part of the core body 61 in the radial direction of the core body 61. Each of the one-end-side magnets 6131 is fitted in each of the one-end-side retention parts 6141, and a seal member (not shown) is attached thereto. The number of the one-end-side retention parts 6141 can be larger than the number of the one-end-side magnets 6131. In this case, the one-end-side magnets 6131 are fitted in selected ones of the one-end-side retention parts 6141.

The other-end-side magnets 6132 are located at the other end of the core body 61. The other-end-side magnets 6132 are located according to a second positional relationship different from the first positional relationship in the circumferential direction of the core body 61. The other-end-side magnets 6132 are located with a certain angular distance from each other in the circumferential direction of the core body 61. In this embodiment, two other-end-side magnets 6132 are arranged at intervals of 180° in the circumferential direction of the core body 61. Further, in this embodiment, the two one-end-side magnets 6131 are located respectively at angular positions different from those of the four other-end-side first recess parts 6152. When the core body 61 is seen from the one end side of the core body 61 and the angular position of the first one of the one-end-side first recess parts 6151 is designated as an angle of 0° in the circumferential direction of the core body 61, first and second ones of the other-end-side magnets 6132 are located at angles of 45° and 225° respectively in the clockwise direction.

Other-end-side retention parts 6142 are formed at the other end of the core body 61 in the same number as the other-end-side magnets 6132. The other-end-side retention parts 6142 function as the magnet retention parts 614 for retaining the magnets 613. The other-end-side retention parts 6142 respectively retain the other-end-side magnets 6132. The other-end-side retention parts 6142 recess inward from the outer peripheral part of the core body 61 in the radial direction of the core body 61. Each of the other-end-side magnets 6132 is fitted in each of the other-end-side retention parts 6142, and a seal member (not shown) is attached thereto. The number of the other-end-side retention parts 6142 can be larger than the number of the other-end-side magnets 6132. In this case, the other-end-side magnets 6132 are fitted in selected ones of the other-end-side retention parts 6142.

Combination of a Wound Body and a Medicine Packing Apparatus

Figure 4:
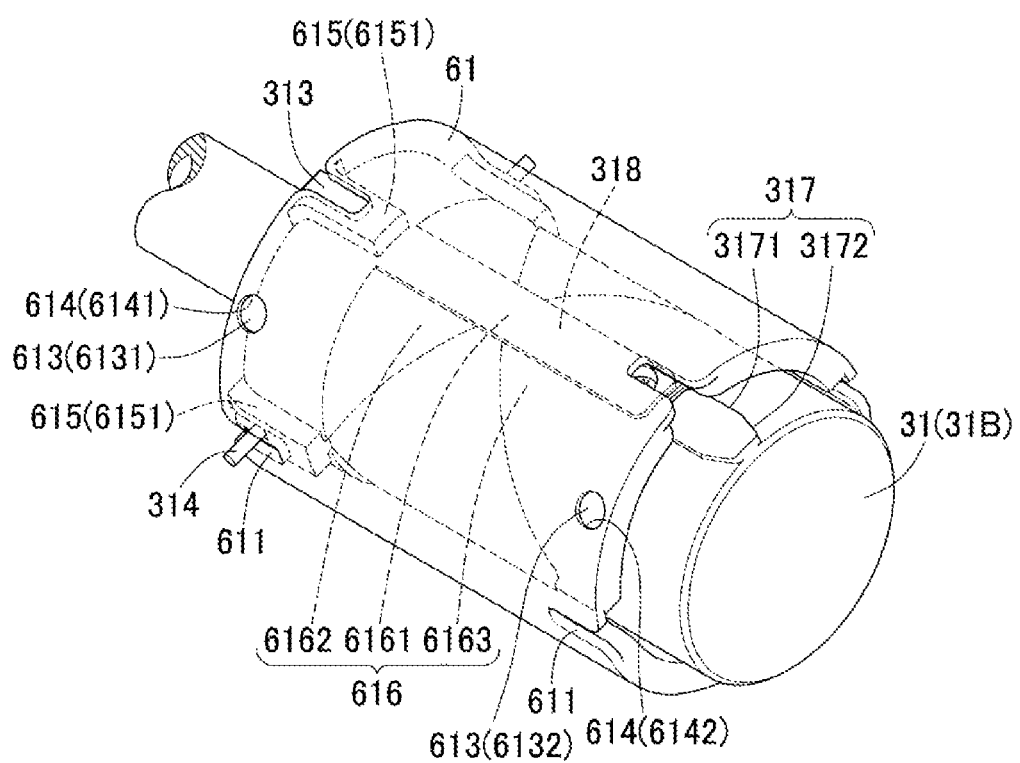
FIG. 4 is a perspective view showing the core body in a state of being mounted to the support shaft of the packing section.

As shown in FIG. 4, the core body 61 is mounted on the outer periphery of the support shaft 31. In the state where the core body 61 is mounted on the outer periphery of the core body 61, the support shaft 31 partially projects from the core body 61. Specifically, the distal end of the support shaft 31 projects from the core body 61. The support shaft 31 may not project from the core body 61 in the state where the core body 61 is mounted on the outer periphery of the support shaft 31.

In the wound body 6, the packing material 62 is wound around the outer periphery of the core body 61 as described above. In FIG. 4, the packing material 62 is omitted. In this embodiment, the packing material 62 is classified into two types based on the sealing temperature. The packing material 62 of a first type is heat-sealed at a first sealing temperature. The packing material 62 of a second type is heat-sealed at a second sealing temperature different from the first sealing temperature.

In this embodiment, the core body 61 is of a single type that is configured to be able to handle the packing material 62 of the two different types. In this embodiment, the orienting direction of the core body 61 relative to the packing material 62 is selected according to the type of the packing material 62. When the packing material 62 of the first type is wound around the core body 61, the orienting direction of the core body 61 relative to the packing material 62 is selected so as to have a fold line of the packing material 62 located on the one end side of the core body 61. Hereinafter, the wound body 6 formed by winding the packing material 62 of the first type in a roll shape will be sometimes referred to as a first wound body 6. When the packing material 62 of the second type is wound around the core body 61, the orienting direction of the core body 61 relative to the packing material 62 is selected to have a fold line of the packing material 62 located on the other end side of the core body 61. Hereinafter, the wound body 6 formed by winding the packing material 62 of the second type in a roll shape will be sometimes referred to as a second wound body 6.

When the first wound body 6 is mounted to the support shaft 31, the core body 61 is mounted on the outer periphery of the support shaft 31 from the one end side of the core body 61. In this case, the first projections 313 are respectively fitted in the one-end-side first recess parts 6151.

Thereby, the support shaft 31 and the core body 61 are integrally rotatable in the circumferential direction of the support shaft 31.

The core body 61 can be mounted to the support shaft 31 at at least one angular position (a plurality of positions, specifically two positions in this embodiment). Specifically, the core body 61 is mounted to the support shaft 31 at an angular position at which the first one of the one-end-side first recess parts 6151 and the first one of the first projections 313 coincide with each other. Or, the core body 61 is mounted to the support shaft 31 at an angular position at which the first one of the one-end-side first recess parts 6151 and the third one of the first projections 313 coincide with each other.

In the state where the core body 61 is mounted on the outer periphery of the support shaft 31, the first projections 313 respectively come into contact with the ends of the one-end-side first recess parts 6151, while the retractable parts 316 are respectively caught by the first catch recess parts 6152A, specifically the step parts 615*a* of the first catch recess parts 6152A. Thus, the core body 61 is prevented from being displaced in the axial direction of the support shaft 31 relative to the outer periphery of the support shaft 31 and thereby the core body 61 can be securely mounted on the outer periphery of the support shaft 31. The contact of the first projections 313 with the ends of the one-end-side first recess parts 6151 allows for prevention of the displacement of the core body 61 relative to the support shaft 31 in a direction in which the core body 61 is mounted to the support shaft 31. The catch of the retractable parts 316 by the first catch recess parts 6152A allows for prevention of the displacement of the core body 61 relative to the support shaft 31 in a direction in which the core body 61 is dismounted from the support shaft 31.

When the second wound body 6 is mounted to the support shaft 31, the core body 61 is mounted on the outer periphery of the support shaft 31 from the other end side of the core body 61. In this case, the first projections 313 are respectively fitted in the other-end-side first recess parts 6152. Thereby, the support shaft 31 and the core body 61 are integrally rotatable in the circumferential direction of the support shaft 31.

The core body 61 can be mounted to the support shaft 31 at at least one angular position (a plurality of positions, specifically two positions in this embodiment). Specifically, the core body 61 is mounted to the support shaft 31 at an angular position at which the first one of the other-end-side first recess parts 6152 and the first one of the first projections 313 coincide with each other. Or, the core body 61 is mounted to the support shaft 31 at an angular position at which the first one of the other-end-side first recess parts 6152 and the third one of the first projections 313 coincide with each other.

In the state where the core body 61 is mounted on the outer periphery of the support shaft 31, the first projections 313 respectively come into contact with the ends of the other-end-side first recess parts 6152, while the retractable parts 316 are respectively caught by the second catch recess parts 6151A, specifically the step parts 615*a* of the second catch recess parts 6151A. Thus, the core body 61 is prevented from being displaced relative to the outer periphery of the support shaft 31 in the axial direction of the support shaft 31 and thereby the core body 61 can be securely mounted on the outer periphery of the support shaft 31. The contact of the first projections 313 with the ends of the other-end-side first recess parts 6152 allows for prevention of the displacement of the core body 61 relative to the support shaft 31 in a direction in which the core body 61 is mounted to the support shaft 31. The catch of the retractable parts 316 by the second catch recess parts 6151A allows for prevention of the displacement of the core body 61 relative to the support shaft 31 in a direction in which the core body 61 is dismounted from the support shaft 31.

The medicine packing apparatus 1 is configured to stop its operation when the movable parts 314 have moved from the retracted position to the advanced position. The positions of the movable parts 314 are detected by a sensor. The medicine packing apparatus 1 is switched between an operative state and an inoperative state on the basis of the detected result of the sensor. The medicine packing apparatus 1 is operable when the movable parts 314 are located at the retracted position. The medicine packing apparatus 1 is inoperable when the movable parts 314 are located at the advanced position.

In the state where the wound body 6 is mounted to the support shaft 31, the movable parts 314 are being pushed by the end face formed by the packing material 62 in a wound state around the wound body 6. Therefore, the movable parts 314 are located at the retracted position. At this time, the medicine packing apparatus 1 is operable.

When the packing material 62 is entirely unwound from the wound body 6, only the core body 61 is left on the support shaft 31. The end face formed by the packing material 62 around the wound body 6 is thus eliminated. Accordingly, the movable parts 314 move in a direction from the proximal end of the support shaft 31 toward the distal end of the support shaft 31. When the first wound body 6 is mounted to the support shaft 31, the movable parts 314 enter the one-end-side cutouts 6111. When the second wound body 6 is mounted to the support shaft 31, the movable parts 314 enter the other-end-side cutouts 6112. Thus, when the movable parts 314 move from the retracted position to the advanced position, the operation of the medicine packing apparatus 1 is stopped.

The medicine packing apparatus 1 is configured to be able to detect the magnetism on at least one of the proximal end side of the support shaft 31 and the distal end side of the support shaft 31 (both sides in this embodiment). A magnetism detection part for detecting the magnetism can be disposed inside the support shaft 31, or can be disposed outside the support shaft 31.

The medicine packing apparatus 1 having such a configuration detects at least one of the plurality of the one-end-side magnets 6131 and a plurality of the other-end-side magnets 6132 (both the one-end-side magnets and the other-end-side magnets in this embodiment). When the first wound body 6 is mounted to the support shaft 31, the one-end-side magnets 6131 are detected on the proximal end side of the support shaft 31, and the other-end-side magnets 6132 are detected on the distal end side of the support shaft 31. When the second wound body 6 has been mounted to the support shaft 31, the other-end-side magnets 6132 are detected on the proximal end side of the support shaft 31, and the one-end-side magnets 6131 are detected on the distal end side of the support shaft 31. The medicine packing apparatus 1 sets the sealing temperature, at which the packing material 62 is heat sealed, on the basis of the detected result. Accordingly, the medicine packing apparatus 1 can heat seal the packing material 62 at a sealing temperature according to the type of the packing material 62.

Mounting of the Wound Body and Dismounting of the Core Body by an Operator

Now, the description will be made for the case where the operator mounts the wound body 6 to the support shaft 31, and the case where the operator dismounts the core body 61 left on the support shaft 31 from the support shaft 31 after the packing material 62 has been entirely unwound from the wound body 6.

Figure 5:
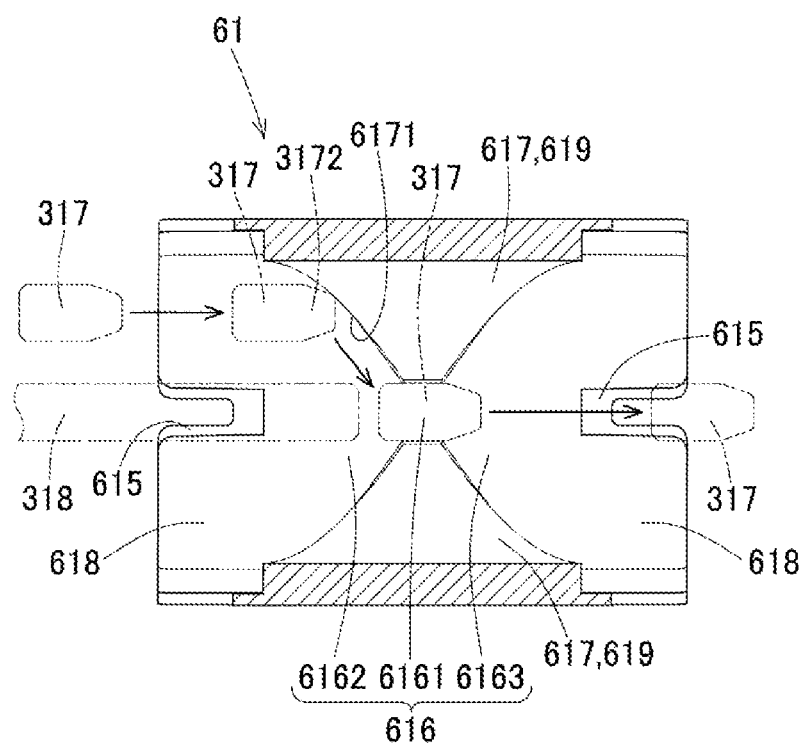
FIG. 5 is an explanatory view showing a state in which the circumferential position of the core body is aligned relative to the support shaft.

As shown in FIG. 5, when the core body 61 is mounted on the outer periphery of the support shaft 31, the circumferential positions of the support shaft 31 and the core body 61 around the support shaft 31 are aligned with each other. In FIG. 5, the second projections 317 and the third projection 318 are shown by two-dot chain line. In FIG. 5, the second projections 317 are shown as moving in the axial direction of the core body 61 relative to the core body 61 for ease of understanding. However, the actual configuration is opposite. That is, the core body 61 actually moves in the axial direction of the support shaft 31 relative to the second projections 317 of the support shaft 31.

When the core body 61 is mounted on the outer periphery of the support shaft 31, the operation may be such that the support shaft 31 is kept unmoved in the circumferential direction while the core body 61 is rotated in the circumferential direction relative to the support shaft 31, or may be such that the core body 61 is kept unmoved in the circumferential direction while the support shaft 31 is rotated in the circumferential direction relative to the core body 61. Or, both the support shaft 31 and the core body 61 may be rotated in the circumferential direction.

Here, the description will be made for the case where the first wound body 6 is mounted to the support shaft 31 for the alignment of the support shaft 31 and the core body 61. When the second wound body 6 is mounted to the support shaft 31, the operation is basically the same as the operation for the case where the first wound body 6 is mounted to the support shaft 31, except for the orienting direction of the core body 61. Thus, the description on the case where the second wound body 6 is mounted to the support shaft 31 will be omitted.

When the first wound body 6 is mounted to the support shaft 31, the operator first holds the first wound body 6 and places this first wound body 6 at a position more on the far side of the distal end of the support shaft 31. The operator directs the one end of the core body 61 toward the support shaft 31. The operator aligns the central axis of the core body 61 with the central axis of the support shaft 31. Thereafter, the operator moves the first wound body 6 relative to the support shaft 31 in the mounting direction.

When the operator moves the first wound body 6 relative to the support shaft 31 in the mounting direction, the one end of the core body 61 is fitted on the distal end of the support shaft 31. The second recess parts 616 are formed along the entire circumference of the core body 61 at the one end of the core body 61. This configuration allows the operator to eliminate the necessity to intentionally align the circumferential positions of the support shaft 31 and the core body 61 around the support shaft 31. Therefore, the mounting operation of the wound body 6 to the support shaft 31 can be facilitated.

A new wound body 6 with an unconsumed packing material 62 wound therearound is heavy. It would be difficult for the operator to perform alignment of the circumferential positions of the support shaft 31 and the core body 61 around the support shaft 31 while holding up the wound body 6. Therefore, the elimination of the necessity to intentionally align the circumferential positions of the support shaft 31 and the core body 61 around the support shaft 31 produces a significant advantage for the operator.

In the course of moving the first wound body 6 in the mounting direction relative to the support shaft 31, the retractable parts 316 come into contact with the inner peripheral surface parts 617. However, the retractable parts 316 are pushed inward in the radial direction of the support shaft 31 by the inner peripheral surface parts 617. Thus, the operator can move the wound body 6 relative to the support shaft 31 in the mounting direction without hindrance.

When the operator further moves the first wound body 6 relative to the support shaft 31 in the mounting direction, the second projections 317 enter the one-end-side leading parts 6162, as shown in FIG. 5. Specifically, the first one of the second projections 317 enters the one-end-side leading part 6162 of the first one of the second recess parts 616, and the second one of the second projections 317 enters the one-end-side leading part 6162 of the second one of the second recess parts 616. Or, the first one of the second projections 317 enters the one-end-side leading part 6162 of the second one of the second recess parts 616, and the second one of the second projections 317 enters the one-end-side leading part 6162 of the first one of the second recess parts 616. Whether each of the second projections 317 enters the one-end-side leading part 6162 of the first one or the second one of the second recess parts is determined according to the positional relationship between the support shaft 31 and the core body 61.

When the operator further moves the first wound body 6 relative to the support shaft 31 in the mounting direction, the second projections 317 are led to the one-end-side leading parts 6162, as shown in FIG. 5. The one-end-side leading parts 6162 are configured to lead the second projections 317 to allow the circumferential positions of the first projections 313 and the one-end-side first recess parts 6151 around the support shaft 31 to be aligned with each other. Accordingly, the operator is not required to carry out any operations other than moving the wound body 6 relative to the support shaft 31 in the mounting direction. The operator can eliminate the necessity to intentionally align the circumferential position of the support shaft 31 with the circumferential position of the core body 61 around the support shaft 31. Thus, the mounting operation of the wound body 6 to the support shaft 31 can be facilitated.

When the operator further moves the first wound body 6 relative to the support shaft 31 in the mounting direction, the second projections 317 enter the guide parts 6161 and are guided to the guide parts 6161. The guide parts 6161 guide the second projections 317 so as to allow the circumferential positions of the first projections 313 and the one-end-side first recess parts 6151 around the support shaft 31 to be kept in alignment with each other. Accordingly, the operator is not required to carry out any operations other than moving the wound body 6 relative to the support shaft 31 in the mounting direction. The operator can eliminate the necessity to intentionally align the circumferential position of the support shaft 31 with the circumferential position of the core body 61 around the support shaft 31. Thus, the mounting operation of the wound body 6 to the support shaft 31 can be facilitated.

When the operator further moves the first wound body 6 relative to the support shaft 31 in the mounting direction, the third projection 318 enters either one of the guide parts 6161 and is guided to either one of the guide parts 6161. When the first one of the second projections 317 has been guided to the first one of the guide parts 6161, the third projection 318 is subsequently guided to this first one of the guide parts 6161. When the first one of the second projections 317 is guided to the second one of the guide parts 6161, the third projection 318 is guided to this second one of the guide parts 6161. The third projection 318 is guided to either one of the guide parts 6161 so as to maintain the alignment between the circumferential positions of the first projections 313 and the one-end-side first recess parts 6151 around the support shaft 31. Accordingly, the operator is not required to carry out any operations other than moving the wound body 6 relative to the support shaft 31 in the mounting direction. The operator can eliminate the necessity to intentionally maintain the alignment between the circumferential positions of the support shaft 31 and the core body 61 around the support shaft 31. Thus, the mounting operation of the wound body 6 to the support shaft 31 can be facilitated.

When the operator further moves the first wound body 6 relative to the support shaft 31 in the mounting direction, the first projections 31 enter the one-end-side first recess parts 6151. When the third projection 318 has been guided to the first one of the guide parts 6161, the first one of the first projections 313 enters the first one of the one-end-side first recess parts 6151 and the second one of the first projections 313 enters the second one of the one-end-side first recess parts 6151, while the third one of the first projections 313 enters the third one of the one-end-side first recess parts 6151 and the fourth one of the first projections 313 enters the fourth one of the one-end-side first recess parts 6151. When the third projection 318 has been guided to the second one of the guide parts 6161, the first one of the first projections 313 enters the third one of the one-end-side first recess parts 6151 and the second one of the first projections 313 enters the fourth one of the one-end-side first recess parts 6151, while the third one of the first projections 313 enters the first one of the one-end-side first recess parts 6151 and the fourth one of the first projections 313 enters the second one of the one-end-side first recess parts 6151.

When the operator further moves the first wound body 6 relative to the support shaft 31 in the mounting direction, the end face formed by the packing material 62 on the first wound body 6 comes into contact with the movable parts 314 located at the advanced position.

When the operator further moves the first wound body 6 relative to the support shaft 31 in the mounting direction, the first projections 313 are fitted in the one-end-side first recess parts 6151. The first projections 313 come into contact with the ends of the one-end-side first recess parts 6151, the retractable parts 316 are released from the contact with the inner peripheral surface parts 617, project outward in the radial direction of the support shaft 31, and are caught by the first catch recess parts 6152A. The movable parts 314 are pushed by the end face formed by the packing material 62 on the first wound body 6 and moved from the advanced position to the retracted position.

Thus, the mounting of the first wound body 6 to the support shaft 31 is completed. Thereafter, the operator unwinds the packing material 62 from the wound body 6, and sets this packing material 62 to the packing material conveyance section 4 and the packing body forming section 5.

When the packing material 62 is entirely unwound from the wound body 6 by the operation of the medicine packing apparatus 1, only the core body 61 is left on the support shaft 31. The operator dismounts the core body 61 from the support shaft 31. When the operator dismounts the core body 61 from the support shaft 31, the operator holds the core body 61 and moves this core body 61 in the dismounting direction. At this time, the retractable parts 316 are being caught by the first catch recess parts 6152A, but the retractable parts 316 are pushed inward in the radial direction of the support shaft 31 by the inner peripheral surface parts 617 of the core body 61 along with the movement of the core body 61. Therefore, the operator can move the core body 61 relative to the support shaft 31 in the dismounting direction without hindrance.

Although the description will be partially repeated, this embodiment is configured as shown in FIG. 2, in which the packing material supply section 3 includes the support shaft 31. The support shaft 31 extends from a non-illustrated mounting base. Apart of the packing material conveyance section 4 (i.e., the tension adjustment mechanism 41 shown in FIG. 1) is also disposed on this mounting base. The support shaft 31 has a substantially columnar shape. The support shaft 31 has the outer peripheral part having a cylindrical shape. The support shaft 31 has the proximal end (left part in FIG. 2) and the distal end (right part in FIG. 2). The proximal end of the support shaft 31 is supported by the mounting base. The support shaft 31 includes the main shaft part 311 having a constant radial dimension, and the proximal end shaft part 312 that is located closer to the proximal end than the main shaft part 311 and that has a larger radial dimension than the main shaft part 311. The step is formed between the main shaft part 311 and the proximal end shaft part 312 as shown in FIG. 2.

The support shaft 31 is rotatably mounted to the mounting base and supports the wound body 6 (core body 61). The support shaft 31 is driven to rotate by the driving unit such as a non-illustrated stepping motor disposed inside the mounting base. The support shaft 31 is rotatable both in the direction in which the packing material 62 is unwound and the direction in which the packing material 62 is wound up. The support shaft 31 is intermittently rotated in response to the supply of the packing material 62 to the packing body forming section 5. The support shaft 31 is cantilever-supported with respect to the mounting base and has the distal end exposed to the outside. Therefore, as shown in FIG. 2, the core body 61 of the wound body 6 is disposed at a position on the exposed side of the support shaft 31, through which the axis of the support shaft 31 extends, and the wound body 6 is placed onto the support shaft 31 from the distal end toward the proximal end in the axial direction so that the wound body 6 (only the core body 61 is shown in FIG. 4) can be mounted to the support shaft 31, as shown in FIG. 4. The wound body 6 is mounted to the support shaft 31 so as not to be relatively rotatable.

The support shaft 31 of this embodiment has a length in the axial direction larger than that of the wound body 6. Therefore, as shown in FIG. 4, a part (i.e., support shaft distal end body 31B) of the support shaft 31 projects from the core body 61 in the mounted state (i.e., the state where the core body 61 is mounted to the support shaft main body 31A). The present invention is not necessarily limited to this configuration. The other end of the core body 61 in the mounted state, which will be later described, can be coincident with the distal end of the support shaft 31.

Apart of the support shaft 31 on the distal end side (i.e., part at which the guide projection 317 is formed), which projects from the core body 61, is the support shaft distal end body 31B that is a separate body from the support shaft main body 31A that is a proximal end part of the support shaft 31 and is mounted to the support shaft main body 31A. This support shaft distal end body 31B can be used in combination with the wound body 6 of this embodiment. The mounting of the support shaft distal end body 31B to the support shaft main body 31A is achieved by means of a fitting engagement used in an engagement structure for mounting a distal end lid of a support shaft of an existing medicine packing apparatus (i.e., structure for mounting the support shaft distal end body 31B after the distal end lid is removed), or bonding to an existing support shaft (the mounting structure is not limited to these, and various mounting forms can be employed). The support shaft main body 31A has an outer peripheral part having a cylindrical shape. The support shaft distal end body 31B in the state of being mounted to the support shaft main body 31A functions as a mount assisting part that is a part of the support shaft 31. According to this configuration, the support shaft 31 of this embodiment can be formed by replacing, for example, a lid member provided at the distal end of a short support shaft with the mount assisting part. The support shaft 31 of this embodiment can be formed by the support shaft distal end body (mount assisting part) 31B to be mounted to the distal end of the support shaft main body 31A, while avoiding a significant modification of an existing medicine packing apparatus. Therefore, the combination of the wound body 6 of this embodiment and the medicine packing apparatus 1 can be realized at a reduced cost. However, when the support shaft 31 is newly produced, it may be configured to employ not a separate structure but an integrated structure in which the support shaft main body 31A and the support shaft distal end body 31B are inseparable from each other. Even for the newly produced support shaft 31, a separate structure can be employed. For example, when a magnetism detector or the like is disposed inside the support shaft 31, the separate structure is useful since the inside of the support shaft 31 can be opened according to needs and circumstances.

As shown in FIG. 2, a plurality of (four in this embodiment) catch projections 313 as the first projections are located at the proximal end shaft part 312 of the support shaft 31. The catch projections 313 are located with a certain distance from each other (at intervals) in the circumferential direction (rotation direction). The catch projections 313 project outward in the radial direction from the outer peripheral surface of the proximal end of the support shaft 31. The catch projections 313 extend in the axial direction from the proximal end edge toward the distal end by a certain distance. Some of the catch projections 313 (every other one of the catch projections 313 in the circumferential direction in this embodiment) respectively include moving parts. In this embodiment, as the moving parts, packing-material-running-out detection pins 314 having a rod shape respectively project from some of the catch projections 313 in the radial direction. Distal ends of the packing-material-running-out detection pins 314 are set to be located radially outward from the outer peripheral surface of the core body 61 when the wound body 6 has been mounted to the support shaft 31. The catch projections 313 provided with the packing-material-running-out detection pins 314 respectively include cutouts 315 extending therethrough in the radial direction and extend in the axial direction.

Each of the packing-material-running-out detection pins 314 is biased toward the distal end in the axial direction (right side in FIG. 4) of the support shaft 31 by a biasing force of a non-illustrated spring disposed inside the support shaft 31. When the wound body 6 with the packing material 62 wound therearound has been mounted to the support shaft 31, the packing-material-running-out detection pins 314 are pushed out to the side by the packing material 62 layered in the radial direction on the outer periphery of the core body 61 and thereby moved toward the proximal end in the axial direction against the spring urging force. The core body 61 of the wound body 6 includes the cutouts 611 extending through the core body 61 in the radial direction and extending in the axial direction in the same manner as the support shaft 31 at parts which become coincide in position with the packing-material-running-out detection pins 314 when the core body 61 is mounted to the support shaft 31. The cutouts 611 include the one-end-side cutouts 6111 located on the one end side of the core body 61, and the other-end-side cutouts 6112 located on the other end side of the core body 61. The one-end-side cutouts 6111 are located at the same positions as those of the second catch recess parts 6151A in the circumferential direction of the core body 61, and each have a cutout shape extending toward the other end of the core body 61. The other-end-side cutouts 6112 are located at the same positions as those of the first catch recess parts 6152A in the circumferential direction of the core body 61, and each have a cutout shape extending from an end face of the other end of the core body 61 toward the one end of the core body 61. The cutouts 611 allow the packing-material-running-out detection pins 314 to respectively enter when the cutouts 611 are positioned at the proximal end of the support shaft 31.

The cutouts 611 are arranged to be coincident in the circumferential direction with the cutouts 315 of the support shaft 31. Therefore, the core body 61 must be rotated in the circumferential direction relative to the support shaft 31 by the operator in order to align the cutouts 611 (this operation will be explained later). When the packing material 62 is unwound from the wound body 6 and run out (that is, only the core body 61 is left), the pushing-out by the packing material 62 is eliminated, and therefore the packing-material-running-out detection pins 314 biased by the springs move toward the distal end in the axial direction and enter the cutouts 611 (see FIG. 4). A sensor or the like detects the entrance of the packing-material-running-out detection pins 314 into the cutouts 611 and thereby detects the run-out of the packing material. For example, the operation of the medicine packing apparatus 1 is stopped based on the detection of the completion of the unwinding of the entire packing material 62 from the wound body 6. Specifically, the packing material supply section 3 can be automatically stopped.

The retractable part 316 projects from the outer peripheral part (specifically, outer peripheral surface) of the support shaft 31. At least one retractable part 316 is disposed (two parts in this embodiment, although another one part is not illustrated). When a plurality of retractable parts 316 are disposed as in this embodiment, these retractable parts 316 are located with a certain distance from each other (at intervals) in the circumferential direction. In this embodiment, the two retractable parts 316 are located at equal intervals in the circumferential direction (that is, at angular intervals of 180°). In this embodiment, the retractable parts 316 are respectively located at the same positions in the circumferential direction as the positions of any ones of the catch projections 313. The retractable parts 316 are respectively located at the same positions in the circumferential direction as the positions of the catch projections 313 that respectively include the packing-material-running-out detection pins 314 and the cutout 315. The retractable parts 316 are respectively located at the positions different from the positions of the guide projections 317 and the sub-guide projection 318 in the circumferential direction. In this embodiment, they are angularly displaced 90° from each other. The retractable parts 316 are projections that have, for example a spherical or a hemispherical shape, are biased radially outward by springs disposed inside the support shaft 31 to project partly from the outer peripheral surface of the support shaft 31. The retractable parts 316 are disposed to be able to be advanced from and retracted into the outer peripheral surface of the support shaft 31.

The retractable parts 316 respectively engage the step parts 615a (see FIG. 3) of those located on the distal end side of the support shaft 31 among the catch recess parts 615 formed to recess outward in the radial direction with respect to the inner peripheral part of the core body 61 (in this embodiment, the catch recess parts are composed of the other-end-side catch recess parts 6152 as the first catch recess parts 6152A, and the one-end-side catch recess parts 6151 as the second catch recess parts 6151A). The retractable parts 316 biased by the springs are caught by the other-end-side catch recess parts 6152 when the core body 61 is mounted to the support shaft 31 from the one end side. The retractable parts 316 biased by the springs are caught by the one-end-side catch recess parts 6151 when the core body 61 is mounted to the support shaft 31 from the other end side. Thereby, in the state where the core body 61 is mounted on the outer periphery of the support shaft 31, the core body 61 is prevented from being displaced relative to the support shaft 31 in a direction from the proximal end toward the distal end of the support shaft 31 by the retractable parts 316 caught by the catch recess parts 615. Thus, the wound body 6 can be securely mounted to the support shaft 31. On the other hand, since the retractable parts 316 are biased by the springs, the core body 61 moves relative to the support shaft 31 by moving the core body 61 in the axial direction by a force stronger than the biasing force of the springs, for example, when the core body 61 is pulled out of the support shaft 31. Therefore, the operation of pulling the core body 61 out of the support shaft 31 can be carried out without hindrance. In a step before the engagement of the retractable parts 316 with the step parts 615a in the course of mounting the core body 61 to the support shaft 31, the retractable parts 316 are in contact with the inner peripheral surface parts 617 of the core body 61. At this time, the retractable parts 316 are pushed by the inner peripheral surface parts 617 and therefore move inward in the radial direction.

At least one guide projection 317 as the second projection 317 (two projections in this embodiment) are formed at the distal end of the support shaft 31 (main shaft part 311). When the plurality of guide projections 317 are formed, these guide projections 317 are located with a certain distance from each other (at intervals) in the circumferential direction. In this embodiment, they are located at an angular distance of 180°. The guide projections 317 project radially outward from the outer peripheral surface of the distal end of the support shaft 31. The projecting positions of the guide projections 317 are the same as the projecting positions of some of the catch projections 313 (two projections among four projections in this embodiment) in the circumferential direction. Specifically, the projecting positions of the guide projections 317 are the same as the projecting positions of the catch projections 313 each of which does not include the packing-material-running-out detection pin 314 and the cut-out 315. The projecting amount of the guide projections 317 projecting in the radially outward direction with respect to the outer peripheral part of the support shaft main body 31A is smaller than that of the catch projections 313.

As shown in FIG. 2, each of the guide projections 317 includes the main body part 3171 having a constant width, and the tapered part 3172 located on the distal end side of the main body part 3171, having a width decreasing toward the distal end and integrally formed with the main body part 3171. The tapered part 3172 has ends in the width direction, which respectively have inclined surfaces. These inclined surfaces each are formed in a straight shape as viewed in the radial direction in this embodiment, but this is not essential. A curved line shape or any other shape can be employed. Also, these inclined surfaces are formed symmetrically with respect to the axial direction in this embodiment, but these may be formed asymmetrically.

The sub-guide projection 318 is formed as the third projection, which projects outward in the radial direction, at a middle position between the proximal end and the distal end of the support shaft 31 on the outer peripheral part of the support shaft 31. At least one sub-guide projection 318 (one projection in this embodiment) is formed on the main shaft part 311 to be continuous with the proximal end of a corresponding one of the guide projections 317. As described above, since two guide projections 317 are formed in this embodiment, the sub-guide projection 318 aligns with one of the guide projections 317 on the proximal end side (guide projection 317 shown in FIG. 2) along the extension line in the axial direction. The catch projections 313 are located on the proximal end side of the sub-guide projection 318.

The sub-guide projection 318 is located at the same position as the guide projections 317 in the circumferential direction around the central axis, and the projecting amount of the sub-guide projection 318 projecting outward in the radial direction with respect to the outer peripheral part of the support shaft 31 is the same as that of the guide projection 317. The sub-guide projection 318 is guided to the guide part 6161 so as to allow the circumferential positions of the catch projections 313 and the catch recess parts 615 around the central axis to be kept in alignment with each other when the core body 61 is mounted on the outer periphery of the support shaft 31.

The inner peripheral surface parts 617 of the core body 61 come into contact with the guide projections 317 by the placement of the core body 61 onto the support shaft 31 so that the alignment of the circumferential position of the core body 61 with the circumferential position of the support shaft 31 around the support shaft 31 can be achieved (description on the alignment of the core body 61 will be later described). FIG. 5 shows the operation for it. In FIG. 5, the guide projections 317 (shown by two-dot chain line) are shown as moving in the axial direction relative to the core body 61 for ease of understanding. However, the actual configuration is opposite to the illustrated configuration. That is, the core body 61 actually moves in the axial direction relative to the guide projections 317. At this time, the circumferential positions of the support shaft 31 and the core body 61 are brought into alignment with each other by the rotational movement relative to each other in the circumferential direction. According to this embodiment, when the placement of the core body 61 onto the support shaft 31 is progressed and then the inner peripheral surface parts 617 of the core body 61 do not contact the guide projections 317 any more, the circumferential edges of the inner peripheral surface parts 617 come into contact with the sub-guide projection 318 so that the operation for alignment of the circumferential position of the core body 61 with the circumferential position of the support shaft 31 can be continued. Therefore, it is possible to securely achieve the alignment during the placement of the core body 61 onto the support shaft 31. During the alignment operation, the support shaft 31 is kept unmoved in the circumferential direction so as to allow the core body 61 to be rotated relative to the support shaft 31, or the core body 61 is kept unmoved in the circumferential direction so as to allow the support shaft 31 to be rotated relative to the core body 61 in the circumferential direction. Or, both the support shaft 31 and the core body 61 are allowed to be respectively rotated in the circumferential direction.

As shown in FIG. 2, the core body 61 of the wound body 6 has a cylindrical shape (circular cylindrical shape) or a tubular shape (circular tubular shape) with a circular cross section taken in the radial direction. The core body 61 has an inner peripheral part having a circular cylindrical shape. As shown in FIG. 1, the packing material 62 is wound around the outer peripheral surface of the core body 61. The outer diameter of the core body 61 is constant in the axial direction. Therefore, no step is formed on the outer peripheral surface of the core body 61 so that the packing material 62 can be wound up with no fold line formed therein. The core body 61 can be mounted on and dismounted from the outer periphery of the support shaft 31 of the packing material supply section 3 by being moved in the axial direction. The core body 61 is mounted on the outer periphery of the support shaft 31 by allowing the circumferential positions of the core body 61 and the support shaft 31 to be aligned with each other around the support shaft 31. The core body 61 has the one end and the other end. The one end is a part close to the support shaft 31 (left back part) in FIG. 2, and the other end is a part far from the support shaft 31 (right front part) in FIG. 2. The core body 61 of this embodiment has a symmetrical shape relative to the center in the axial direction, in which the shape of the one end is the same as the shape of the other end except for magnet retention parts 614. The symmetrical shape allows the core body 61 to be mounted to the support shaft 31 from any of the one end side and the other end side. Thus, the permanent magnets (magnets 613) retained by the magnet retention parts 614 allow the operator to know whether the core body 61 is mounted to the support shaft 31 with the one end or the other end of the core body 61 being directed to the support shaft 31 so that at least two different types of the packing material 62 can be dealt by the single core body 61 having the same shape. Thus, the control for manufacturing the wound body 6 can be easily performed.

As a regular direction (mounting direction) for the core body 61, there are two cases depending on the type of the packing material 62 to be wound up, namely one case where the core body 61 is mounted to the support shaft 31 from the one end side, and another case where the core body 61 is mounted to the support shaft 31 from the other end side. At the time of mounting, the core body 61 is moved in the axial direction from the distal end toward the proximal end of the support shaft 31. The core body 61 has the cutouts 611 at both ends. With the core body 61 mounted to the support shaft 31, the cutouts 611 are located at the positions corresponding to the packing-material-running-out detection pins 314 projecting outward in the radial direction from the support shaft 31. The cutouts 611 extend through the core body 61 in the radial direction and define spaces opening at the end faces of the core body 61. Each of the packing-material-running-out detection pins 314 is movable in the axial direction within each corresponding one of the spaces. This movement is done after the packing material 62 has been unwound from the wound body 6 and no packing material 62 remains on the wound body 6 (FIG. 4 shows the state after the movement).

The core body 61 includes the magnet retention parts 614 that retain permanent magnets (magnets 613) combined to correspond to a magnetic detecting part such as a magnetic sensor that is included in the packing material supply section 3 for identifying the wound body 6. In this embodiment, two magnet retention parts 614 are located at the one end of the core body 61 at intervals of 90° in the circumferential direction. Two magnet retention parts 614 are located at the other end of the core body 61 at intervals of 180° in the circumferential direction. Thus, the positions at which the magnet retention parts 614 are located are different between the one end and the other end. Therefore, when the permanent magnets (magnets 613) are arranged at all the magnet retention parts 614, the positional relationship of the permanent magnets (magnets 613) arranged at the both ends are different from each other.

The permanent magnets (magnets 613) may be arranged at a selected number of the magnet retention parts 614 among all the magnet retention parts 614. The identification of the wound body 6 specifically means the identification of a material of the packing material 62, which relates to the sealing temperature for proper bonding when the packing material 62 is bonded by heat sealing. The identification may be made by the magnetic detecting part that detects the number of the magnet retention parts 614 at which the permanent magnets (magnets 613) are arranged, the polarity or the strength of the magnetic force of the permanent magnets (magnets 613). The magnet retention parts 614 are not needed in a medicine packing apparatus, in which the identification of the wound body 6 is made by any other m other than the magnet, for example, electromagnetic detection by using, for example, IC chips such as the RFID tag enabling the wireless identification, or optical detection by the two-dimensional code, or in a medicine packaging apparatus, in which the magnetic detecting part is removed or disabled by the modification. In the configuration of performing the electromagnetic detection, the RFID tag or the like is arranged in the inner space of the core body 61, for example. The RFID tag or the like may be arranged on the inner peripheral surface or outer peripheral surface of the core body 61.

The one-end-side magnets 6131 are located at the one end of the core body 61 in the circumferential direction of the core body 61 according to a first positional relationship. On the other hand, the other-end-side magnets 6132 are located at the other end of the core body 61 in the circumferential direction according to a second positional relationship different from the first positional relationship. In the state where the core body 61 is mounted on the outer periphery of the support shaft 31, the medicine packing apparatus 1 is configured such that the magnetic detecting part detects at least one of a plurality of the one-end-side magnets 6131 and a plurality of the other-end-side magnets 6132 and sets the sealing temperature at which the packing material 62 is heat sealed.

The inner periphery of the core body 61 includes the catch recess parts 615 as the first recess parts, guide recess parts 616 as the second recess parts, and the inner peripheral surface parts 617. A pair of the catch recess parts 615, a pair of the guide recess parts 616, and a pair of the inner peripheral surface parts 617 are disposed in the circumferential direction. These pairs can be located at equal intervals in the circumferential direction. In this embodiment, four pairs of the catch recess parts 615 are located at equal intervals in the circumferential direction, and two pairs of the guide recess parts 616 and two pairs of the inner peripheral surface parts 617 are located at equal intervals in the circumferential direction. However, it is possible to dispose only one pair, or locate a plurality of pairs of each of them at unequal intervals. These parts 615 to 617 are located symmetrically in the axial direction (with reference to the center in the axial direction).

Each of the catch recess parts 615 includes an one-end-side catch recess part 6151 as the one-end-side first recess part formed in the inner periphery on the one end side of the core body 61, and an other-end-side catch recess part 6152 as the other-end-side first recess part formed in the inner periphery on the other end side of the core body 61. Apart of each of the catch recess parts 615 which is located close to the proximal end in the state where the core body 61 is mounted to the support shaft 31 engages the catch projection 313 of the support shaft 31 to enable transmission of a rotational force in the circumferential direction between the core body 61 and the support shaft 31. That is, in the state where the core body 61 is mounted on the outer periphery of the support shaft main body 31A, the support shaft main body 31A and the core body 61 are integrally rotatable around the central axis of the outer peripheral part of the support shaft main body 31A by the engagement between the catch projections 313 and the catch recess parts 615. The number of the catch recess parts 615 is the same as the number of the catch projections 313 of the support shaft 31. The number of the pairs each comprising the guide recess part 616 and the inner peripheral surface part 617 is the same as the number of the guide projections 317 of the support shaft 31. However, the number of the catch recess parts 615 can be larger than the number of the catch projections 313 of the support shaft 31. The number of pairs each comprising the guide recess part 616 and the inner peripheral surface part 617 can be larger than the number of the guide projections 317.

The guide recess parts 616 are located in the inner periphery of the core body 61 to extend along the axial direction. The guide recess parts 616 have an inner diameter larger than the outer diameter of the support shaft 31. The recessing amount of the guide recess parts 616 recessing outward in the radial direction with respect to the inner peripheral part of the core body 61 (more specifically, the inner peripheral surface, still more specifically, the inner peripheral surface of the inner peripheral surface part 617 or the large thickness part 619) is smaller than the recessing amount of the catch recess parts 615 (i.e., the one-end-side catch recess parts 6151, the other-end-side catch recess parts 6152). Therefore, it is possible to prevent deterioration of the strength of the core body 61 due to the recesses. The guide recess parts 616 are formed along the entire circumference of the core body 61 on each of the one end and the other end of the core body 61 (parts 6162a and 6163a shown in FIG. 3). Therefore, when the core body 61 is inserted around the support shaft distal end body 31B, it is not necessary to align the circumferential position of the core body 61 with the circumferential position of the support shaft distal end body 31B around the central axis. Thus, easy operation can be realized. The guide recess parts 616 engage the guide projections 317 and the sub-guide projection 318 when the core body 61 is mounted to the support shaft 31, thereby aligning the circumferential position of the core body 61 with the circumferential position of the support shaft 31 around the support shaft 31. That is, when the core body 61 is mounted on the outer periphery of the support shaft main body 31A, the guide projections 317 and the guide recess parts 616 engage the guide recess parts 616, thereby aligning the circumferential positions of the guiding projections 317 and the sub-guide projection 318 with the circumferential positions of the guide recess parts 616 around the central axis of the outer peripheral part of the support shaft main body 31A. Each of the guide recess parts 616 includes the positioning part 6161 that has a constant width (dimension in the circumferential direction) and extends in the axial direction, and a leading part that is continuous with the one end side or the other end side of the positioning part 6161, and has a width (dimension in the circumferential direction) increasing as it advances from the center toward the one end or the other end in the axial direction. This leading part includes the one-end-side leading part 6162 located close to the one end of the core body 61, and the other-end-side leading part 6163 located close to the other end of the core body 61. The width of the positioning part 6161 is substantially the same as the width of the guiding projections 317. Specifically, the width of the positioning part 6161 is larger than (slightly larger than) the width of the guiding projections 317 to the extent which allows for the movement of the guiding projections 317 through the positioning part 6161 in the axial direction of the core body 61.

Each of the leading parts 6162 and 6163 has a dimension in the circumferential direction decreasing as it advances from the one end or the other end toward the center part in the axial direction, so that the core body 61 is moved in the circumferential direction according to this decrease (see FIG. 5 for the one-end-side leading part 6162; FIG. 5 shows the opposite relationship between the core body 61 and the guiding projections 317 regarding the movability and the immovability to the actual relationship). The catch recess parts 615 of the core body 61 coincide with the catch projections 313 of the support shaft 31. Thus, the core body 61 is rotated relative to the support shaft 31 to have their circumferential positions aligned with each other.

Thus, when the core body 61 is mounted on the outer periphery of the support shaft 31, the leading parts 6162 and 6163 lead the guiding projections 317 to allow the circumferential positions of the catch projections 313 to be aligned with the circumferential positions of the one-end-side catch recess parts 6151 or the other-end-side catch recess parts 6152 around the central axis (when seen from the opposite viewpoint, the leading parts 6162 and 6163 are led by the guiding projections 317).

The parts 6162a and 6163a of the inner peripheral part of the core body 61 which respectively correspond to the position of the one end of the core body 61 and the position of the other end of the core body 61 (see FIG. 3) do not produce an effect of moving the core body 61 in the circumferential direction by the contact with the guiding projections 317. The parts 6162a and 6163a produce an effect of facilitating the mounting of the core body 61 to the support shaft 31. The inner diameter of the parts 6162a and 6163 is larger than the outer diameter of the support shaft 31. That is, the inner diameter of the parts 6162a and 6163a does not have a tight relationship, that is, has a "loose" relationship with the outer diameter of the support shaft 31. Therefore, the insertion of the wound body 6 (core body 61) onto the support shaft 31 can be easily made compared with the configuration lacking such a clearance. Since the wound body 6 having the core body 61 on which the packing material 62 is wound is heavy (in particular, a new wound body 6 is heavy because of no consumption of the packing material 62), the facilitation of the insertion is a great advantage for the user of the medicine packing apparatus 1. This effect is also an effect produced by the later-described small thickness parts 618.

The parts 6162a and 6163a can be said as "free areas" for allowing for the rotation of the core body 61 without limitation. The positioning part 6161 can be said as "limitation areas" in which the rotation of the core body 61 is limited to the extent which makes it substantially impossible (specifically, a clearance exists to the extent which allows for a positional displacement of the guide recess parts 616 of the core body 61 in the axial direction relative to the guiding projections 317 and the sub-guide projection 318 of the support shaft 31). The leading parts 6162 and 6163 can be said as "transition areas" in which the range in which the core body 61 is rotatable is smaller in the central side in the axial direction than that in the one end side and the other end side in the axial direction. The free area, the transition area, and the limitation area of each of the guide recess parts 616 are continued in this order from the one end side to the center in the axial direction. Further, the transition area and the free area are continued in this order from the center in the axial direction to the other end in the axial direction.

The inner peripheral surface parts 617 are parts adjacent to the guide recess parts 616 in the circumferential direction. The inner peripheral surface parts 617 have a larger thickness (i.e., a larger dimension in the radial direction) than that of the guide recess parts 616. Each of the inner peripheral surface parts 617 is located at the center in the axial direction of the core body 61 and have ends that respectively do not reach the edges on the both end sides of the core body 61 in the axial direction and that are located between the center in the axial direction and the edges on the both end sides in the axial direction of the core body 61. Each of the inner peripheral surface parts 617 has an edge having a shape corresponding to the shape of the leading parts 6162 and 6163, and has a dimension in the circumferential direction that increases as it advances from the one end side toward the center in the axial direction and decreases as it advances from the center toward the other end in the axial direction. Thus, each of the inner peripheral surface parts 617 has a shape symmetrical in the axial direction with respect to the center in the axial direction.

The surface of each of the inner peripheral surface parts 617 is a curved face having a constant curvature in the circumferential direction. The curvature the surface in the circumferential direction of each of the inner peripheral surface parts 617 is the same (substantially the same) as the curvature in the circumferential direction of the outer peripheral surface of the support shaft 31. Since the surface of each of the inner peripheral surface parts 617 is a curved face having a wide area, each of the inner peripheral surface parts 617 comes into surface contact with the outer peripheral surface of the support shaft 31 when the core body 61 is mounted to the support shaft 31. For example, in the configuration in which projections are formed on the inner peripheral surface of the support shaft to extend in the axial direction, the core body comes in into line contact with the outer peripheral surface of the support shaft. In this arrangement, a phenomenon called "winding and tightening" sometimes occurs due to the stress (i.e., force causing shrinkage in the longitudinal direction) remaining in the packing material after the winding operation in the manufacturing the wound body, the surrounding temperature or humidity. This "winding and tightening" may cause deformation (distortion) to the main part of the core body that is in a floating state relative to the supporting shaft. Contrarily to this, in this embodiment, since the surface of each of the inner peripheral surface parts 617 comes into surface contact with the outer peripheral surface of the support shaft 31, it is possible to reduce the possibility of causing the aforementioned deformation (distortion) to the core body 61.

Since the inner peripheral surface parts 617 have a large thickness and the guide recess parts 616 have a small thickness, a step is formed between each of the inner peripheral surface parts 617 and each of the guide recess parts 616. That is, the edges in the circumferential direction of the positioning part 6161 of each of the guide recess parts 616 and the leading parts 6162 and 6163 are defined by each of the inner peripheral surface parts 617. Each of the inner peripheral surface parts 617 has core-body-side inclined faces 6171 defining the edges in the width direction (circumferential direction) of the leading parts 6162 and 6163 of the guide recess parts 616 (see FIG. 3).

When the core body 61 including the catch recess parts 615, the guide recess parts 616, and the inner peripheral surface parts 617 is to be mounted to the support shaft 31 from the one end side, the leading parts 6162 of the core body 61 are first positioned to face the guiding projections 317 of the support shaft 31. Further, when the core body 61 is moved in the axial direction, the positions of the positioning parts 6161 of the core body 61 are changed relative to the guiding projections 317 (see position changes shown by the arrows in FIG. 5).

The positioning parts 6161 are also the guide parts for guiding the guiding projections 317. Each of the positioning parts 6161 as the guide parts is located at the center in the axial direction of the core body 61, that is, located between the one-end-side leading part 6162 and the other-end-side leading part 6163, is continuous with the leading parts 6162 and 6163, and is configured to guide the guiding projection 317 so as to allow the circumferential positions of the catch projections 313 and the catch recess parts 615 (i.e., one-end-side catch recess parts 6151 or the other-end-side catch recess parts 6152) to be maintained in alignment with each other around the outer periphery part of the support shaft main body 31A when the core body 61 is mounted on the outer periphery of the support shaft main body 31A. Thereby, when the core body 61 is mounted to the support shaft main body 31A, it is not necessary to intentionally maintain the state where the circumferential position of the support shaft main body 31A is aligned with the circumferential position of the core body 61 around the central axis. Thus, this allows for ease of the alignment operation.

The one-end-side leading part 6162 has a width (dimension in the circumferential direction) decreasing as it advances from the one end toward the other end of the core body 61 until it reaches the center in the axial direction. Thereby, when the core body 61 is mounted on the outer periphery of the support shaft main body 31A, the one-end-side leading part 6162 is configured to lead the guiding projection 317 to allow the circumferential positions of the catch projections 313 and the catch recess parts 615 to be aligned with each other around the central axis of the outer periphery part of the support shaft main body 31A. According to this configuration, it is not necessary to intentionally align the circumferential position of the support shaft main body 31A and the circumferential position of the core body 61 with each other around the central axis. This allows for ease of the operation. The sub-guide projection 318 is configured to lead the core body 61 from the center to the other end in the axial direction as the mounting operation proceeds from the one end toward the other end of the core body 61.

When the guiding projection 317 is located at an end in the circumferential direction of the corresponding one-end-side leading part 6162, the edge of the one-end-side leading part 6162, that is, the core-body-side inclined face 6171 on the one end side contacts the guiding projection 317. Thereby, the guiding projection 317 is led to a position at which it coincides with the positioning part 6161 of the core body 61. When the core body 61 is moved further in the axial direction, the guiding projection 317 is released from the positioning part 6161 of the core body 61. Subsequently, in place of the guiding projection 317, the sub-guide projection 318 formed continuously with the proximal end of the guiding projection 317 is led to a position at which it coincides with the positioning part 6161 (see FIG. 5). As a result of the leading by the guiding projection 317 and the sub-guide projection 318, the catch projections 313 engage the catch recess parts 615. When the core body 61 is moved further in the axial direction, the guiding projections 317 partially project outward from the other end of the core body 61 and thereby the catch projections 313 completely engage the catch recess parts 615 to finally come into a state as shown in FIG. 5.

The edge (core-body-side inclined face 6171) of the one-end-side leading part 6162 sometimes comes into contact with the inclined face of the tapered part 3172 of the guiding projection 317 (see FIG. 5). Since the core-body-side inclined face 6171 that is the edge of the one-end-side leading part 6162 has substantially the same degree of inclination as that of the inclined face of the tapered part 3172 of the guiding projection 317. Therefore, the contact therebetween can be smoothly performed. The same is applicable to the other-end-side leading part 6163.

According to the core body 61 of this embodiment, the mounting of the core body 61 to the support shaft 31 can be easily performed by the guide recess parts 616, and the strength of the core body 61 can be secured by the inner peripheral surface parts 617.

The core body 61 includes the small thickness parts 618 and the large thickness parts 619. The small thickness parts 618 are disposed in the inner periphery of the core body 61 respectively on the one end side and the other end side in the axial direction. Each of the small thickness parts 618 is fitted on the proximal end shaft part 312 of the support shaft 31 in the state where the core body 61 is mounted to the support shaft 31. The large thickness parts 619 are fitted on the main shaft part 311 of the support shaft 31 in the state where the core body 61 is mounted to the support shaft 31. The large thickness parts 619 have a thickness larger than the small thickness parts 618. The small thickness parts 618 correspond to the aforementioned guide recess parts 616, and the large thickness parts 619 correspond to the aforementioned inner peripheral surface parts 617. The small thickness parts 618 are formed for the purpose different from that of the guide recess parts 616, while the formation area of the small thickness parts 618 in the inner periphery of the core body 61 is the same as that of the guide recesses 616. The formation areas of the small thickness parts 618 and the guide recess parts 616 can be differentiated from each other. The large thickness parts 619 are formed for the purpose different from that of the aforementioned inner peripheral surface parts 617, while the formation area of the large thickness parts 619 in the inner periphery of the core body 61 is the same as that of the inner peripheral surface parts 617. The formation areas of the large thickness parts 619 and the inner peripheral surface parts 617 can be differentiated from each other.

Recycling of the Used Core Body

The core body 61 can be repeatedly used many times by recycling the core body 61 after the core body 61 is used up. This can contribute to, for example, saving resources. The recycling is realized by winding a new packing material 62 around the used core body 61 recovered from the user of the medicine packing apparatus 1. The winding of the new packing material 62 around the core body 61 to be recycled makes it possible to manufacture a new wound body 6. For the smooth recovery, it may be configured such that the wound body 6 is delivered to the user while the core body 61 of it is rented to the user, and the user returns the core body 61 thereafter. This can promote the recovery of the core body 61.

Figure 19:
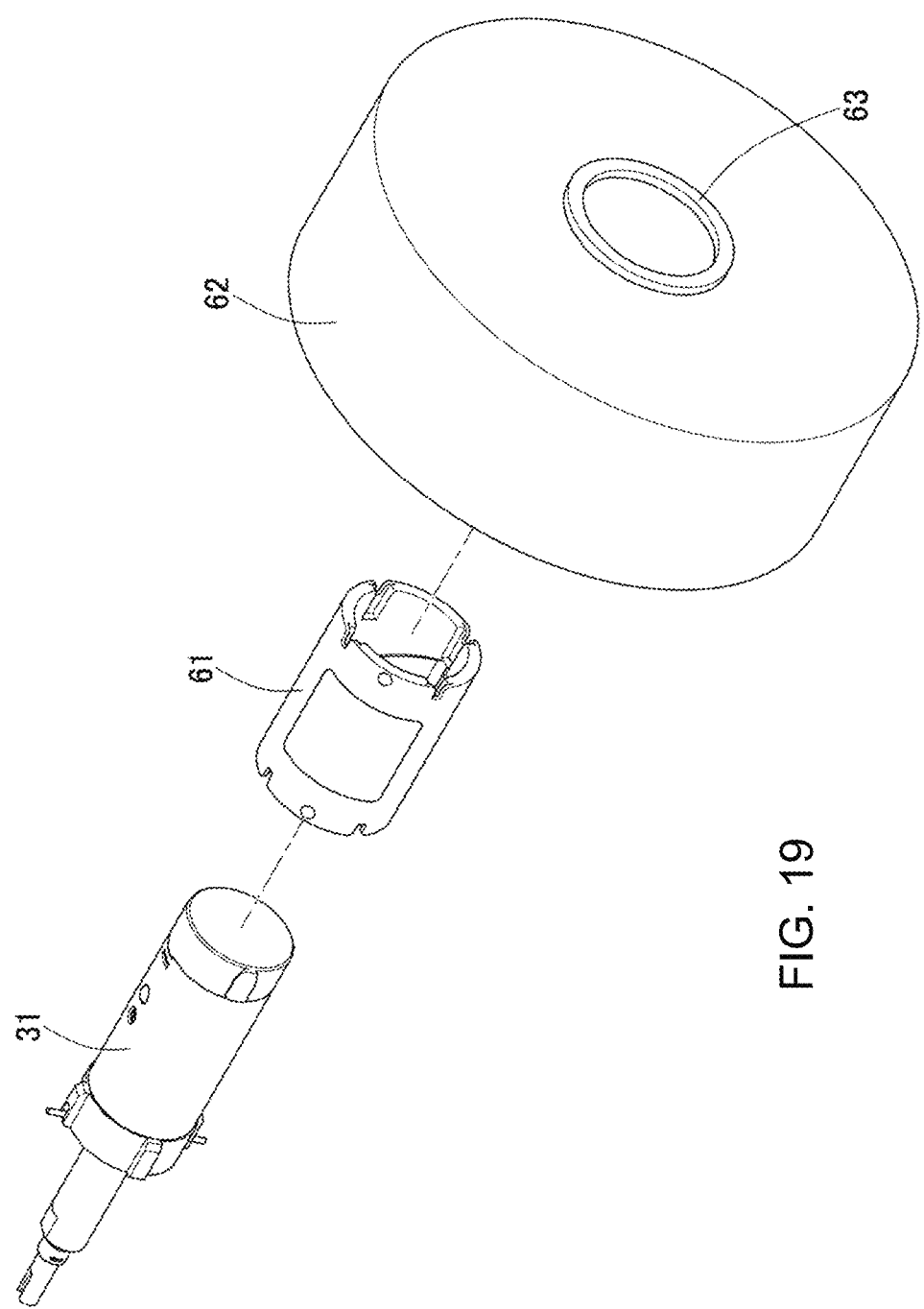
FIG. 19 is a perspective view showing the core body of the modified example in conjunction with the support shaft and the packing material in a roll shape.

The winding of a new packing material 62 around the used core body 61 can be made by, for example, a method, in which the new packing material 62 is wound around a separate core body (e.g., paper cylinder) 63 having an inner diameter larger than the outer diameter of the core body 61 (see FIG. 19, for example), and a thus previously produced packing material roll (replacement wound body) is mounted to the used core body 61. When employing this method, it is possible to adjust the difference in dimension between the outer diameter of the used core body 61 and the inner diameter of the separate core body by interposing a spacer such as a rubber ring between the used core body 61 and the separate core body.

The production of the new wound body 6 can be made by a supplier of the wound body 6, or the works relating to the production can be made by the user according to the instructions sent from the supplier of the wound body 6 to the user. In the latter case, the used core body 61 is not recovered but remains possessed by the user's site. The instructions from the supplier of the wound body 6 to the user may be explicitly or implicitly made. Examples of the implicit instructions include transferring, selling or assignment of the replacement wound body.

Possibility to Modify the Embodiment

Although the description was made on the one embodiment of the present invention, the present invention is not necessarily limited to the above embodiment and can be subjected to various modifications within the gist of the present invention.

Figure 6:
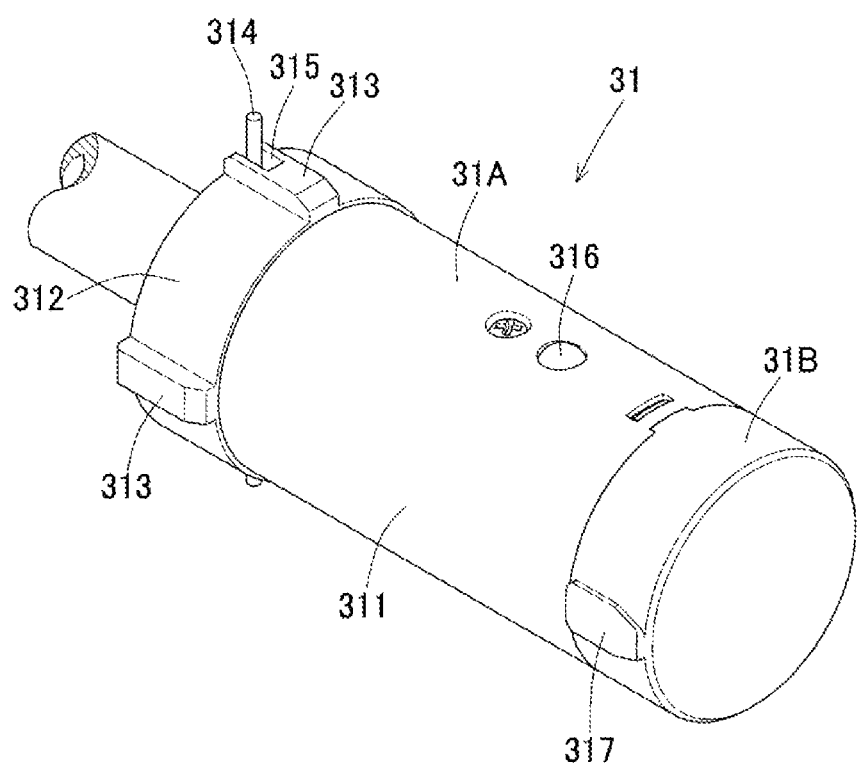
FIG. 6 is a perspective view showing one example (first Ex.) according to another form of the support shaft.
Figure 7:
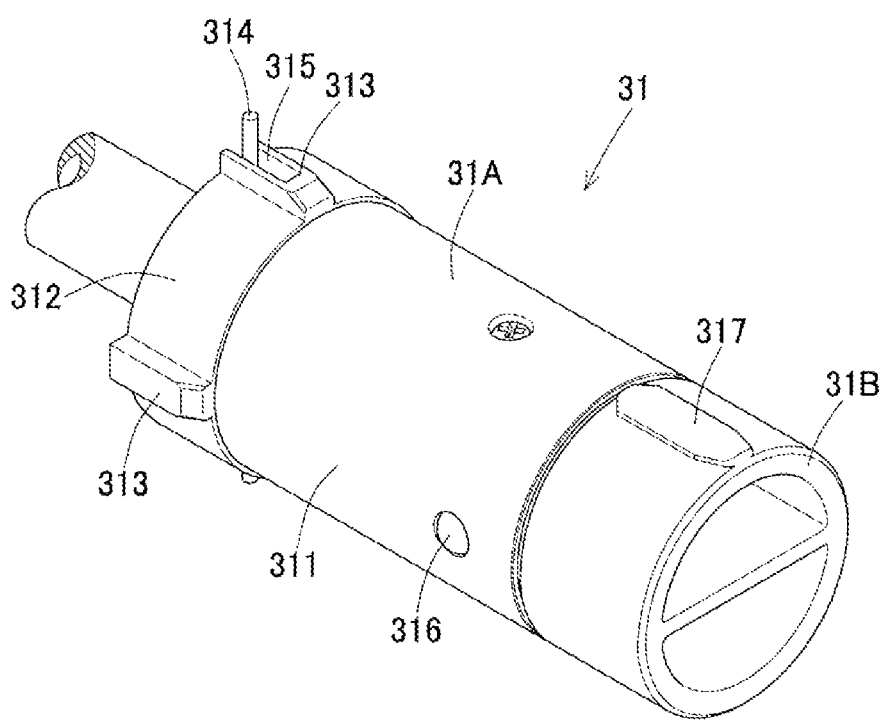
FIG. 7 is a perspective view showing one example (second Ex.) according to still another form of the support shaft.
Figure 8:
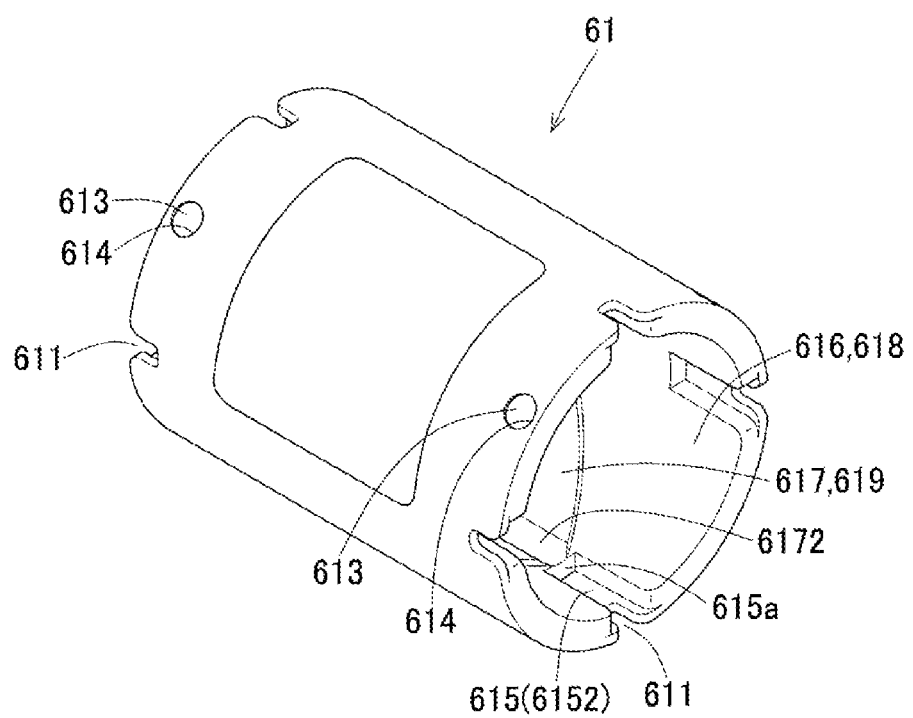
FIG. 8 is a reduced perspective view of another example (modified example) of the core body as seen from the front, plane and left sides.
Figure 9:
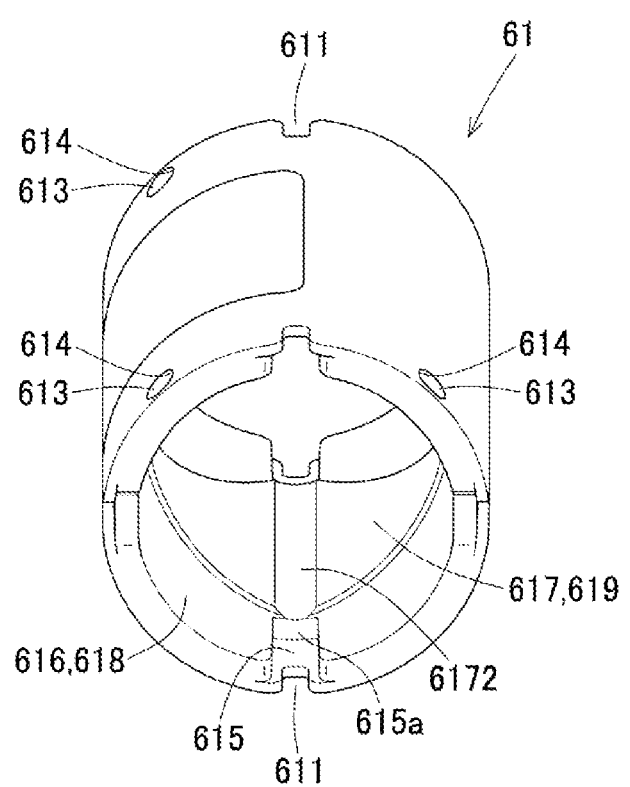
FIG. 9 is a reduced perspective view of the modified example as seen from the front and plane sides
Figure 10:
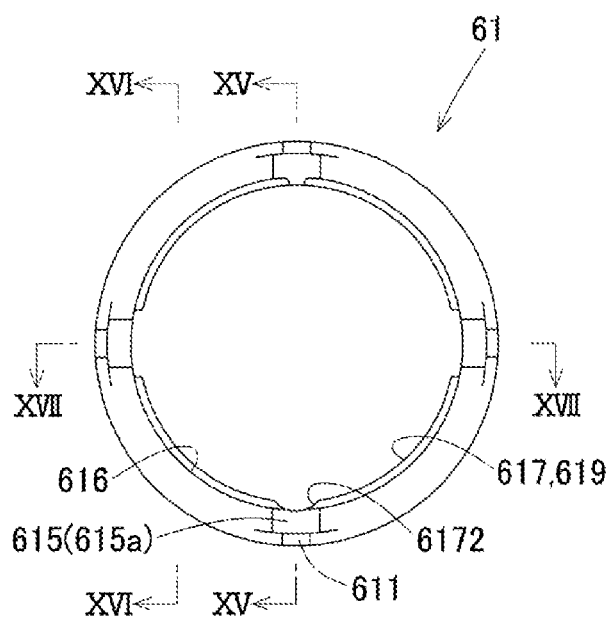
FIG. 10 is a front view of the modified example.
Figure 11:
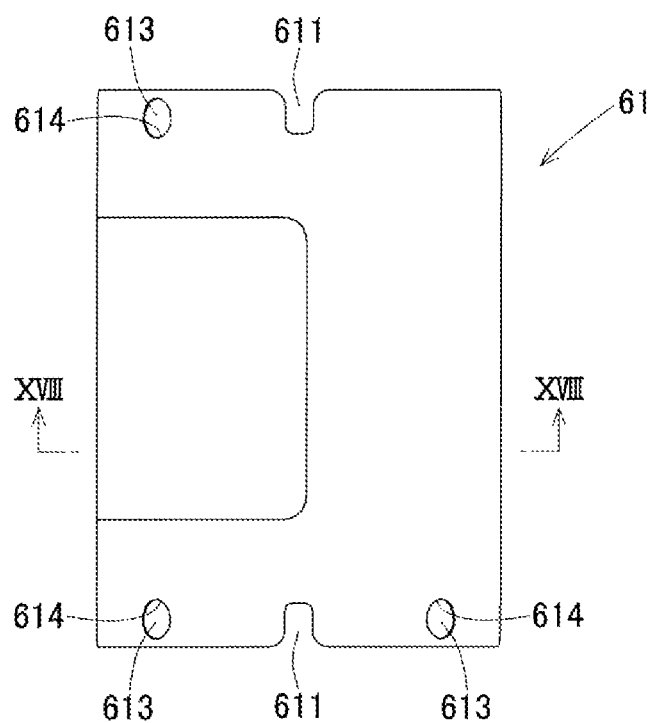
FIG. 11 is a plan view of the modified example.
Figure 12:
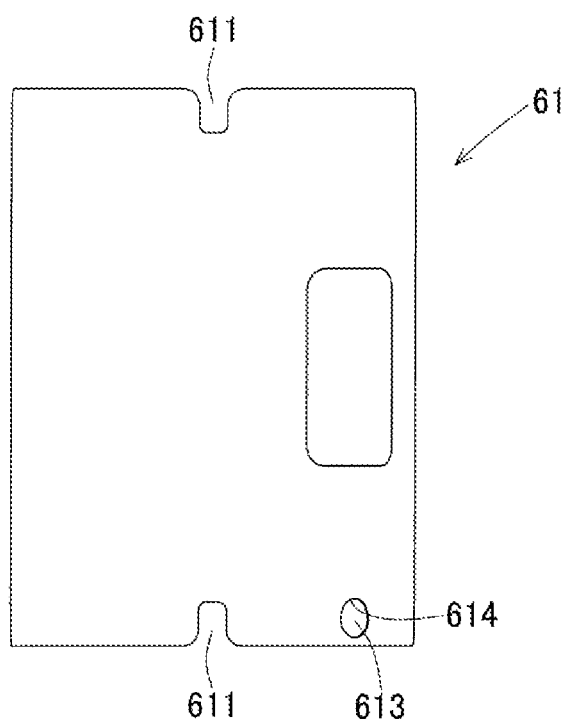
FIG. 12 is a bottom view of the modified example.
Figure 13:
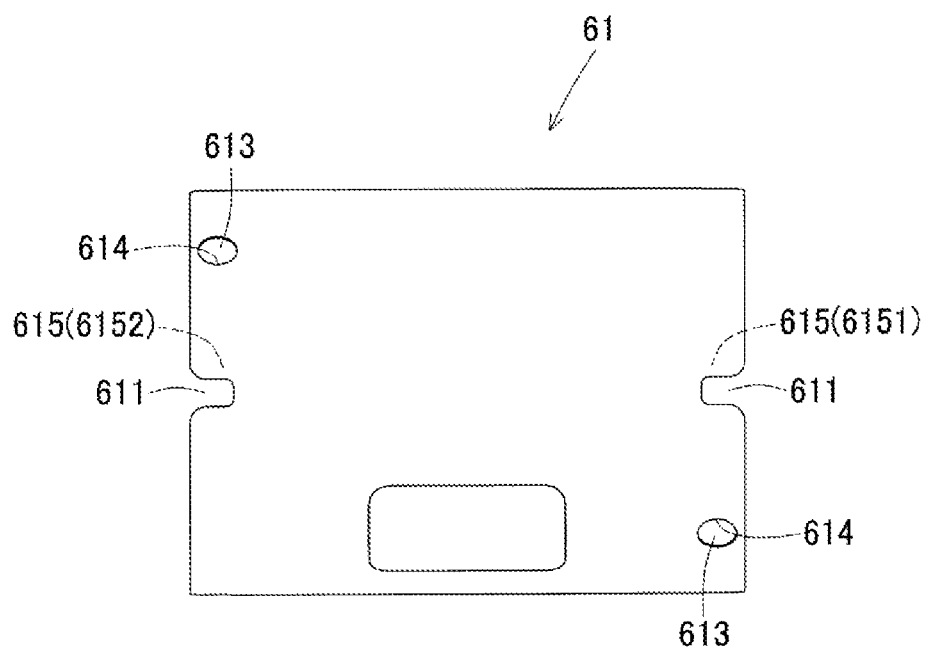
FIG. 13 is a right side view of the modified example.
Figure 14:
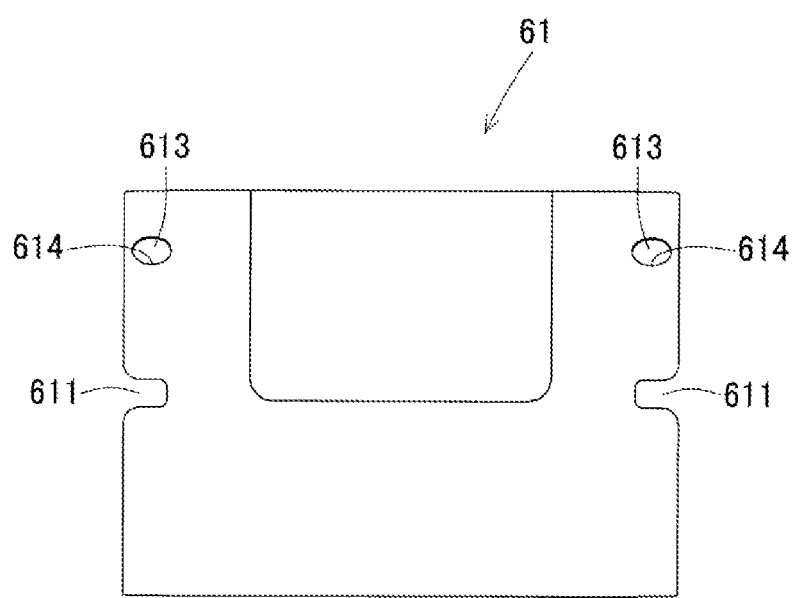
FIG. 14 is a left side view of the modified example.
Figure 15:
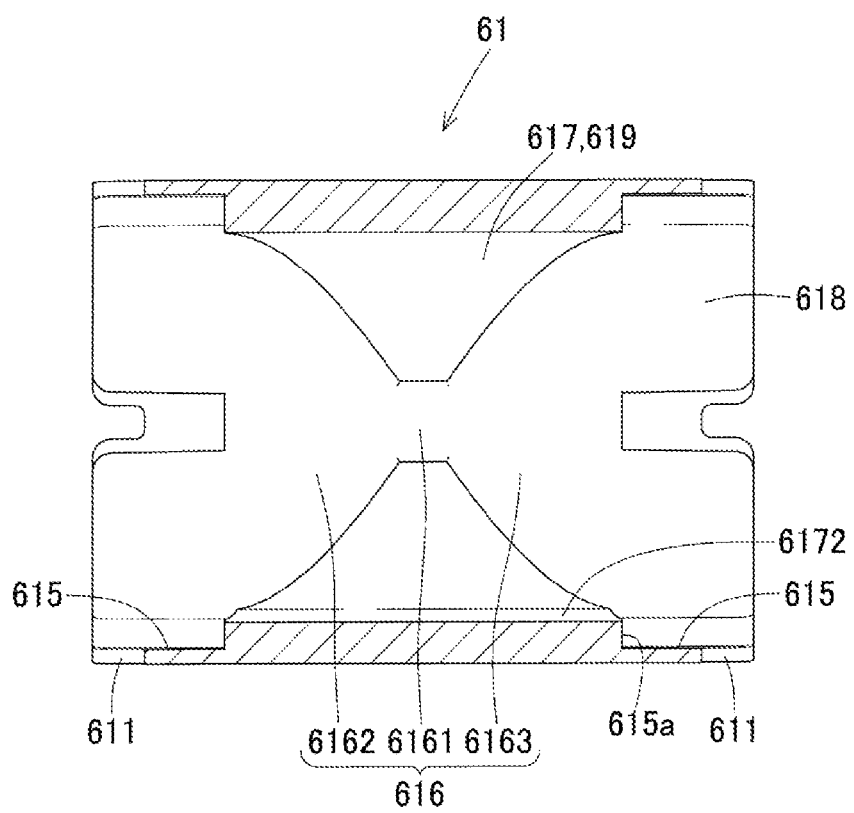
FIG. 15 is an enlarged cross sectional view of the modified example taken along a line XV-XV in FIG. 10.
Figure 16:
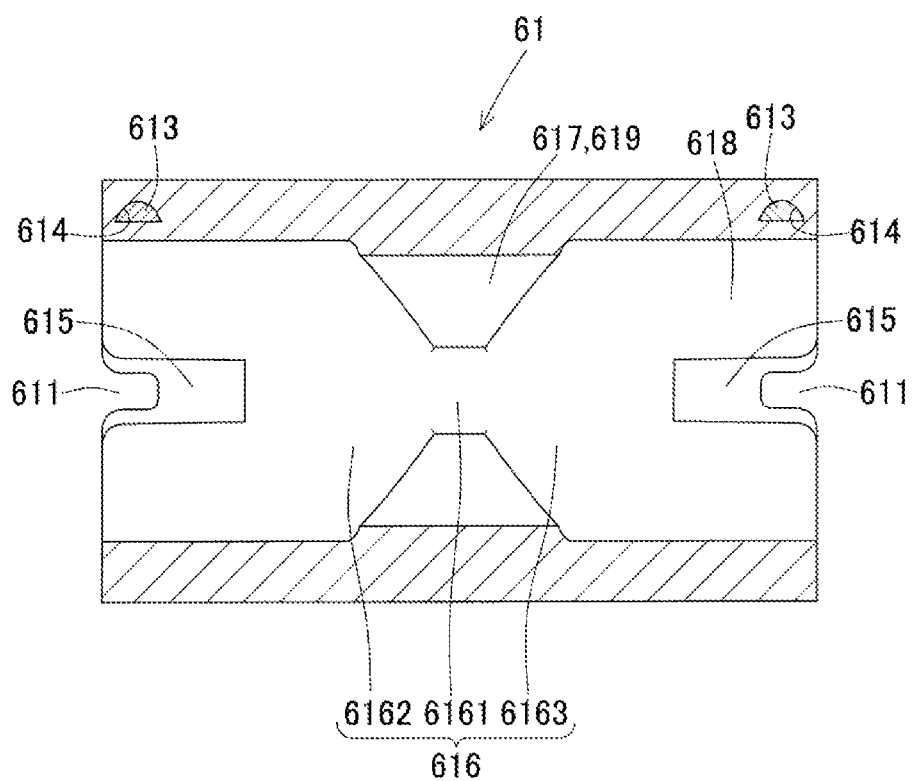
FIG. 16 is an enlarged cross sectional view of the modified example taken along a line XVI-XVI in FIG. 10.
Figure 17:
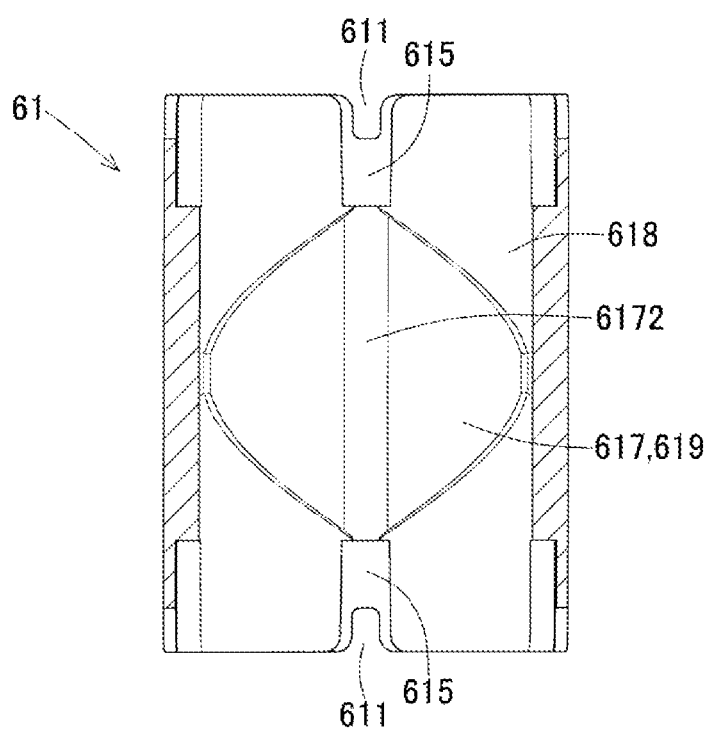
FIG. 17 is a cross sectional view of the modified example along a line XVII-XVII in FIG. 10.
Figure 18:
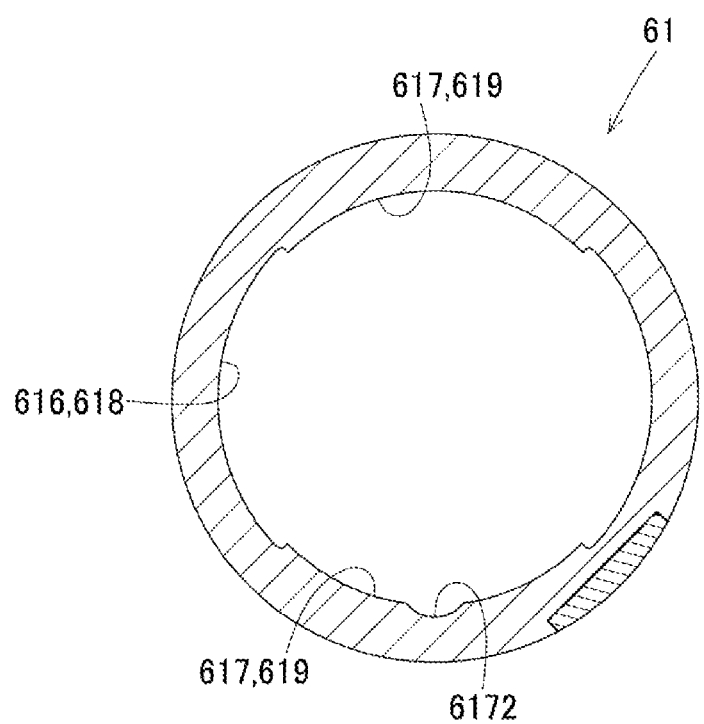
FIG. 18 is an enlarged end face view of the modified example taken along a line XVIII-XVIII in FIG. 11.

The support shaft 31 may have various forms as shown in, for example, FIG. 6 and FIG. 7. The support shaft 31 as shown in FIG. 6 and FIG. 7 is basically the same as the support shaft 31 of the above embodiment, but is different from the support shaft 31 of the above embodiment in that the third projection (sub-guide projection) 318 is not provided. That is, the support shaft 31 can be configured to eliminate the sub-guide projection 318.

The support shaft 31 having this form is available by modifying a support shaft of an existing medicine packing apparatus. The support shaft of the existing medicine packing apparatus includes the support shaft main body 31A and a distal end cover. The distal end cover is mounted to the distal end of the support shaft main body 31A to cover the distal end of the support shaft main body 31A. The support shaft 31 of FIG. 6 and FIG. 7 is in a state where the distal end cover is removed from the distal end of the support shaft main body 31A and the support shaft distal end body (mount assisting device) 31B is mounted to the distal end of the support shaft main body 31A. The support shaft 31 having such a configuration can be produced without the necessity to greatly modify the support shaft of the existing medicine packing apparatus. Thus, it is possible to realize the combination of the wound body 6 of this embodiment and the medicine packing apparatus 1 at low cost.

The core body 61 may have forms like modified examples shown in FIG. 8 to FIG. 18. That is, at least one third recess part 6172 (one recess in this example) may be formed in the inner peripheral part of the core body 61. The retractable part 316 engages the third recess part 6172 when the core body 61 is mounted on the outer periphery of the support shaft 31. The third recess part 6172 is located at an intermediate position between the one end of the core body 61 and the other end of the core body 61 and recesses outward in the radial direction. The recessing amount of the third recess part 6172 recessing outward in the radial direction with respect to the inner peripheral part of the core body 61 (specifically, the inner peripheral surface of the core body 61) is smaller than the recessing amount of the one-end-side catch recess parts 6151 and the other-end-side catch recess parts 6152. Therefore, it is possible to prevent lowering of the strength of the core body 61 due to the formation of the third recess part 6172.

The third recess part 6172 is located at a certain angular position in the circumferential direction of the core body 61. In this embodiment, the third recess part 6172 is located at an angular position displaced 90° from one of the two guide recess parts 616 in the circumferential direction of the core body 61. When the core body 61 is seen from the one end side (left end side in FIG. 8) of the core body 61 and the angular position of the first one of the one-end-side first recess parts 6151 is designated as an angle of 0° in the circumferential direction of the core body 61, the third recess part 6172 is located at an angle of 270° in the clockwise direction.

When the operator moves the wound body in the mounting direction relative to the support shaft 31, the third recess part 6172 guides the retractable part 316 so as to allow the circumferential positions of the first projections 313 and the first recess parts 615 (specifically, the one-end-side first recess parts 6151 or the other-end-side first recess parts 6152) to be kept in alignment with each other around the support shaft 31. Thus, the operator is required only to move the wound body 6 in the mounting direction relative to the support shaft 31 even in the case where the support shaft 31 is not provided with the sub-guide projection 318. The operator is not required to intentionally maintain the alignment between the circumferential positions of the support shaft 31 and the core body 61 around the support shaft 31. Therefore, the mounting operation of the wound body to the support shaft 31 can be facilitated.

The shape of a part of the core body 61 of this modified example close to the center in the axial direction is not limited to those as shown in FIG. 8 to FIG. 18 and can be various shapes. The core body 61 can be configured to eliminate the magnet retention parts 614. Although the two inner peripheral surface parts 617 are provided as described above, the shape of one of the inner peripheral surface parts 617 in which the third recess part 6172 is not provided can be various shapes.

Regardless of whether the magnet retention parts 614 are provided or not, the core body 61 can be configured to eliminate the magnets 613. In such a case, the medicine packing apparatus 1 can be configured to set the sealing temperature using a different means. Also, in this case, the orienting direction of the core body 61 relative to the packing material 62 may be any direction. The fold line of the packing material 62 can be located close to the one end of the core body 61 or the other end of the core body 61. In this case, since the orienting direction is not limited to a certain direction, the manufacturing of the wound body 6 can be facilitated.

According to the aforementioned embodiment, the circumferential positions of the first projections 313 and the first recess parts 615 (the one-end-side catch recess parts 6151 or the other-end-side catch recess parts 6152) are aligned with each other around the central axis by the engagement between the second projections 317 and the second recess parts 616. Therefore, even for the wound body 6 with the packing material 62 wound therearound, the alignment of the circumferential positions can be easily made. Thus, the mounting operation of the wound body 6 to the support shaft 31 can be facilitated.

REFERENCE SIGNS LIST

1: Medicine packing apparatus
2: Packing section
3: Packing material supply section
31: Support shaft
31A: Support shaft main body
31B: Support shaft distal end body
311: Main shaft part
312: Proximal end shaft part
313: Catch projection, first projection
314: movable part, packing-material-running-out detection pin
316: Retractable part
317: Guiding projection, second projection
318: Sub-guide projection, third projection
4: Packing material conveyance section
5: Packing body forming section
6: Wound body
61: Core body
611: Cutout
6111: One-end-side cutout
6112: Other-end-side cutout
613: Magnet
6131: One-end-side magnet
6132: Other-end-side magnet
614: Magnet retention part
6141: One-end-side retaining part
6142: Other-end-side retaining part
615: Catch recess, first recess part
6151: One-end-side first recess part, second catch recess part, one-end-side catch recess part
6152: Other-end-side first recess part, first catch recess part, other-end-side catch recess part,
616: second recess part, guide recess part
6161: Guide part, positioning part
6162: One-end-side leading part
6163: Other-end-side leading part
617: Inner peripheral surface part
618: Small thickness part
619: Large thickness part
62: Packing material

The invention claimed is:

1. A wound body formed by winding a long sheet, wherein the wound body is supportable by a support shaft,
the support shaft comprises a cylindrical outer peripheral part having a proximal end and a distal end, and is configured to be rotatable around a central axis of the cylindrical outer peripheral part,
the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection,
the wound body comprises a core body having a cylindrical shape, and the long sheet wound around an outer periphery of the core body,
the core body comprises a cylindrical inner peripheral part having one end and an other end,
the cylindrical inner peripheral part comprises a one-end-side first recess part located at the one end and recessing into the core body in the radial direction, an other-end-side first recess part located at the other end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the one-end-side first recess part and the other-end-side first recess part, the core body is mountable on an outer periphery of the support shaft from the one end side of the core body or the other end side of the core body, and from the distal end side of the support shaft, the support shaft and the core body are integrally rotatable around the central axis by engagement of the first projection with the one-end-side first recess part or the other-end-side first recess part in a state where the core body is mounted on the outer periphery of the support shaft, and a circumferential position of the first projection around the central axis is aligned with a circumferential position of the one-end side first recess part or the other-end-side first recess part around the central axis by the engagement of the second projection with the second recess part when the core body is mounted on the outer periphery of the support shaft.

2. The wound body according to claim 1, wherein the second recess part is formed along an entire circumference in a circumferential direction of the core body at each of the one end of the core body and the other end of the core body.

3. The wound body according to claim 1, wherein the second recess part comprises a one-end-side leading part configured to lead the second projection when the core body is mounted on the outer periphery of the support shaft from the one end side, and an other-end-side leading part configured to lead the second projection when the core body is mounted on the outer periphery of the support shaft from the other end side, and each of the one-end-side leading part and the other-end-side leading part is configured to lead the second projection to allow the circumferential position of the first projection around the central axis to be aligned with the circumferential position of the one-end-side first recess part or the other-end-side first recess part around the central axis when the core body is mounted on the outer periphery of the support shaft.

4. The wound body according to claim 3, wherein the one-end-side leading part is located close to the one end of the core body, and the other-end-side leading part is located close to the other end of the core body.

5. The wound body according to claim 3, wherein the second recess part comprises a guide part that guides the second projection, and the guide part is located between the one-end-side leading part and the other-end-side leading part, and is configured to guide the second projection to allow the circumferential position of the first projection around the central axis to be kept in alignment with the circumferential position of the one-end-side first recess part or the other-end-side first recess part around the central axis when the core body is mounted on the outer periphery of the support shaft.

6. The wound body according to claim 5, wherein the cylindrical outer peripheral part of the support shaft comprises a third projection that is located at an intermediate position between the proximal end of the support shaft and the distal end of the support shaft and that projects outward in the radial direction, the third projection is located at a same position as the second projection in the circumferential direction around a central axis, a projecting amount of the third projection projecting outward in the radial direction with respect to the cylindrical outer peripheral part of the support shaft is the same as that of the second projection, and the third projection is guided by the guide part to allow the circumferential position of the first projection around the central axis to be kept in alignment with a circumferential position of the one-end-side first recess part or the other-end-side first recess part around the central axis when the core body is mounted on the outer periphery of the support shaft.

7. The wound body according to claim 1, wherein the support shaft comprises a retractable part that is disposed to be retractable and extendable relative to the cylindrical outer peripheral part of the support shaft, and that is biased outward in the radial direction, the retractable part is located at a position different from the second projection in a circumferential direction around the central axis, the cylindrical inner peripheral part of the core body comprises a first catch recess part that recesses into the core body in the radial direction and is configured to catch the retractable part when the core body has been mounted on a outer periphery of the support shaft from the one end side of the core body, and a second catch recess part that recesses into the core body in the radial direction and is configured to catch the retractable part when the core body has been mounted on the outer periphery of the support shaft from the other end side of the core body, and the retractable part is caught by the first catch recess part or the second catch recess part in the state where the core body is mounted on the outer periphery of the support shaft, so that the core body is prevented from being displaced relative to the support shaft in a direction from the proximal end of the support shaft toward the distal end of the core body.

8. A wound body formed by winding a long sheet, comprising:

a core body having a cylindrical shape, and the long sheet wound around an outer periphery of the core body, wherein the core body comprises a cylindrical inner peripheral part having one end and an other end, the cylindrical inner peripheral part comprises a one-end-side first recess part located at the one end and recessing into the core body in a radial direction, an other-end-side first recess part located at the other end and recessing into the core body in the radial direction, and a second recess part located to extend from the one end to the other end and recessing into the core body in the radial direction, in which a recessing amount of the second recess part recessing into the core body in the radial direction with respect to the inner peripheral part is smaller than that of the one-end-side first recess part and the other-end-side first recess part, the core body is mountable on an outer periphery of a rotatable support shaft from the one end side or the other end side of the core body, the core body is configured such that, with the core body mounted on the outer periphery of the rotatable support shaft, the core body is rotatable integrally with the rotatable support shaft by engagement of the one-end-side first recess part or the other-end-side first recess part with a first projection that is located at a proximal end of the rotatable support shaft, and such that, when the core body is mounted on the outer periphery of the rotatable support shaft, a circumferential position of the first projection is aligned with a circumferential position of the one-end-side first recess part or the other-end-side first recess part around the rotatable support shaft by engagement of the second recess part with a second projection that is located at a distal end of the rotatable support shaft.

9. A core body for a wound body that is used for the wound body formed by winding a long sheet, wherein
the wound body is supportable by a support shaft,
the support shaft comprises a cylindrical outer peripheral part having a proximal end and a distal end, and is configured to be rotatable around a central axis of the cylindrical outer peripheral part,
the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection,
the core body for the wound body has a cylindrical shape, is configured to allow the long sheet to be wound around an outer periphery of the core body, and comprises a cylindrical inner peripheral part having one end and an other end,
the cylindrical inner peripheral part comprises an one-end-side first recess part located at the one end and recessing outward into the core body in the radial direction, an other-end-side first recess part located at the other end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the one-end-side first recess part and the other-end-side first recess part,
the core body for the wound body is mountable on an outer periphery of the support shaft from the one end side of the core body for the wound body or the other end side of the core body for the wound body, and from the distal end side of the support shaft,
the support shaft and the core body for the wound body are integrally rotatable around the central axis by engagement of the first projection with the one-end-side first recess part or the other-end-side first recess part in a state where the core body for the wound body is mounted on the outer periphery of the support shaft, and
a circumferential position of the first projection around the central axis is aligned with a circumferential position of the one-end side first recess part or the other-end-side first recess part around the central axis by engagement of the second projection with the second recess part when the core body for the wound body is mounted on the outer periphery of the support shaft.

10. A combination of a wound body and a support shaft, the combination comprising
the wound body formed by winding a long sheet, and the support shaft that supports the wound body, wherein
the support shaft comprises a cylindrical outer peripheral part having a proximal end and a distal end, and is configured to be rotatable around a central axis of the cylindrical outer peripheral part,
the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection,
the wound body comprises a core body having a cylindrical shape, and the long sheet wound around an outer periphery of the core body,
the core body comprises a cylindrical inner peripheral part having one end and an other end,
the cylindrical inner peripheral part comprises a one-end-side first recess part located at the one end and recessing into the core body in the radial direction, an other-end-side first recess part located at the other end and recessing into the core body in the radial direction, and a second recess part located to extend from the one end to the other end and recessing into the core body in the radial direction, in which a recessing amount of the second recess part recessing into the core body outward in the radial direction with respect to the cylindrical inner peripheral part is smaller than that of the one-end-side first recess part and the other-end-side first recess part,
the core body is mountable on an outer periphery of the support shaft from the one end side of the core body or the other end side of the core body, and from the distal end side of the support shaft,
the support shaft and the core body are integrally rotatable around the central axis by engagement of the first projection with the one-end-side first recess part or the other-end-side first recess part in a state where the core body is mounted on the outer periphery of the support shaft, and
a circumferential position of the first projection around the central axis is aligned with a circumferential position of the one-end side first recess part or the other-end-side first recess part around the central axis by engagement of the second projection with the second recess part when the core body is mounted on the outer periphery of the support shaft.

11. A combination of a wound body and a medicine packing apparatus, the combination comprising
the wound body formed by winding a long sheet, and the medicine packing apparatus that comprises a support shaft for supporting the wound body, and that is configured to pack a medicine using the long sheet wound off from the wound body supported by the support shaft, wherein
the support shaft comprises a cylindrical outer peripheral part having a proximal end and a distal end, and is configured to be rotatable around a central axis of the cylindrical outer peripheral part,
the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection, the wound body comprises a core body having a cylindrical shape, and the long sheet wound around an outer periphery of the core body, the core body comprises a cylindrical inner peripheral part having one end and an other end, the cylindrical inner peripheral part comprises a one-end-side first recess part located at the one end and recessing into the core body in the radial direction, an other-end-side first recess part located at the other end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the one-end-side first recess part and the other-end-side first recess part, the core body is mountable on an outer periphery of the support shaft from the one end side of the core body or the other end side of the core body, and from the distal end side of the support shaft, the support shaft and the core body are integrally rotatable around the central axis by engagement of the first projection with the one-end-side first recess part or the other-end-side first recess part in a state where the core body is mounted on the outer periphery of the support shaft, and a circumferential position of the first projection around the central axis is aligned with a circumferential position of the one-end-side first recess part or the other-end-side first recess part around the central axis by engagement of the second projection with the second recess part when the core body is mounted on the outer periphery of the support shaft.

12. The combination of the wound body and the medicine packing apparatus according to claim 11, wherein the support shaft comprises a movable part that is located at the first projection, that is configured to project outward in the radial direction from the core body in the state where the core body is mounted on the outer periphery of the support shaft, that is disposed to be movable in an axial direction of the central axis, and that is biased in a direction from the proximal end of the support shaft toward the distal end of the support shaft, the core body comprises a one-end-side cutout that is located at a same position as the one-end-side first recess part in a circumferential direction of the core body in the one end of the core body, that has a cutout shape extending from an end face of the one end of the core body toward the other end of the core body, and that is configured to allow the movable part to enter the one-end-side cutout, the core body further comprises an other-end-side cutout that is located at the same position as the other-end-side first recess part in the circumferential direction of the core body in the other end of the core body, that has a cutout shape extending from an end face of the other end of the core body toward the one end of the core body, and that is configured to allow the movable part to enter the other-end-side cutout, and the medicine packing apparatus is configured to stop an operation of the medicine packing apparatus when the movable part enters the one-end-side cutout or the other-end-side cutout.

13. The combination of the wound body and the medicine packing apparatus according to claim 11, wherein a plurality of one-end-side magnets are located at the one end of the core body according to a first positional relationship in a circumferential direction of the core body, a plurality of other-end-side magnets are located at the other end of the core body according to a second positional relationship different from the first positional relationship in the circumferential direction of the core body, and the medicine packing apparatus is configured to detect at least one of the plurality of the one-end-side magnets and the plurality of the other-end-side magnets to set a sealing temperature at which the long sheet is heat sealed, in the state where the core body is mounted on the outer periphery of the support shaft.

14. A wound body formed by winding a long sheet, wherein the wound body is supportable by a support shaft, the support shaft comprises a cylindrical outer peripheral part having a proximal end and a distal end, and is configured to be rotatable around a central axis of the cylindrical outer peripheral part, the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection, the wound body comprises a core body having a cylindrical shape, and the long sheet wound around an outer periphery of the core body, the core body comprises a cylindrical inner peripheral part having one end and an other end, the cylindrical inner peripheral part comprises a first recess part located at the one end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the first recess part, the core body is mountable on an outer periphery of the support shaft from the one end side of the core body and from the distal end side of the support shaft, the support shaft and the core body are integrally rotatable around the central axis by engagement of the first projection with the first recess part in a state where the core body is mounted on the outer periphery of the support shaft, a circumferential position of the first projection around the central axis is aligned with a circumferential position of the first recess part around the central axis by engagement of the second projection with the second recess part when the core body is mounted on the outer periphery of the support shaft, and the second recess part comprises a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part comprises a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the cylindrical outer peripheral part of the support shaft comprises a third projection that is located at an intermediate position between the proximal end of the support shaft and the distal end of the support shaft and that projects outward in the radial direction, the third projection is located at a same position as the second projection in a circumferential direction around the central axis, a projecting amount of the third projection projecting outward in the radial direction with respect to the cylindrical outer peripheral part of the support shaft is a same as that of the second projection, and the third projection is guided by the guide part to allow the circumferential positions of the first projection and the first recess part around the central axis to be kept in alignment with each other when the core body is mounted on the outer periphery of the support shaft.

15. The wound body according to claim 14, wherein the second recess part is formed along an entire circumference in a circumferential direction of the core body at the one end of the core body.

16. The wound body according to claim 14, wherein the leading part is located close to the one end of the core body.

17. The wound body according to claim 14, wherein
the support shaft comprises a retractable part that is disposed to be retractable and extendable relative to the cylindrical outer peripheral part of the support shaft, and that is biased outward in the radial direction, the retractable part is located at a position different from the second projection in the circumferential direction around the central axis, the cylindrical inner peripheral part of the core body comprises a catch recess part that recesses into the core body in the radial direction and is configured to catch the retractable part, and the retractable part is caught by the catch recess part in the state where the core body is mounted on the outer periphery of the support shaft, so that the core body is prevented from being displaced relative to the support shaft in a direction from the proximal end of the support shaft toward the distal end of the core body.

18. A core body for a wound body that is used for the wound body formed by winding a long sheet, wherein
the wound body is supportable by a support shaft,
the support shaft comprises a cylindrical outer peripheral part having a proximal end and a distal end, and is configured to be rotatable around a central axis of the cylindrical outer peripheral part, the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection, the core body for the wound body has a cylindrical shape, is configured to allow the long sheet to be wound around an outer periphery of the core body, and comprises a cylindrical inner peripheral part having one end and an other end, the cylindrical inner peripheral part comprises a first recess part located at the one end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the first recess part, the core body for the wound body is mountable on an outer periphery of the support shaft from the one end side of the core body for the wound body and from the distal end side of the support shaft, the support shaft and the core body for the wound body are integrally rotatable around the central axis by engagement of the first projection with the first recess part in a state where the core body for the wound body is mounted on the outer periphery of the support shaft, a circumferential position of the first projection around the central axis is aligned with a circumferential position of the first recess part around the central axis by engagement of the second projection with the second recess part when the core body for the wound body is mounted on the outer periphery of the support shaft, the second recess part comprises a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part comprises a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the cylindrical outer peripheral part of the support shaft comprises a third projection that is located at an intermediate position between the proximal end of the support shaft and the distal end of the support shaft and that projects outward in the radial direction, the third projection is located at a same position as the second projection in a circumferential direction around the central axis, a projecting amount of the third projection projecting outward in the radial direction with respect to the cylindrical outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

19. A combination of a wound body and a support shaft, the combination comprising
the wound body formed by winding a long sheet, and the support shaft that supports the wound body, wherein
the support shaft comprises a cylindrical outer peripheral part having a proximal end and a distal end, and is configured to be rotatable around a central axis of the cylindrical outer peripheral part, the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection, the wound body comprises a core body having a cylindrical shape, and the long sheet wound around an outer periphery of the core body, the core body comprises a cylindrical inner peripheral part having one end and an other end, the cylindrical inner peripheral part comprises a first recess part located at the one end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the first recess part, the core body is mountable on an outer periphery of the support shaft from the one end side of the core body and from the distal end side of the support shaft, the support shaft and the core body are integrally rotatable around the central axis by engagement of the first projection with the first recess part in a state where the core body is mounted on the outer periphery of the support shaft, a circumferential position of the first projection around the central axis is aligned with a circumferential position of the first recess part around the central axis by engagement of the second projection with the second recess part when the core body is mounted on the outer periphery of the support shaft, the second recess part comprises a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part comprises a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the cylindrical outer peripheral part of the support shaft comprises a third projection that is located at an intermediate position between the proximal end of the support shaft and the distal end of the support shaft and that projects outward in the radial direction, the third projection is located at a same position as the second projection in a circumferential direction around the central axis, a projecting amount of the third projection projecting outward in the radial direction with respect to the cylindrical outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

20. A combination of a wound body and a medicine packing apparatus, the combination comprising the wound body formed by winding a long sheet, and the medicine packing apparatus that comprises a support shaft for supporting the wound body, and that is configured to pack a medicine using the long sheet wound off from the wound body supported by the support shaft, wherein the support shaft comprises a cylindrical outer peripheral part having a proximal end and a distal end, and is configured to be rotatable around a central axis of the cylindrical outer peripheral part, the cylindrical outer peripheral part comprises a first projection located at the proximal end and projecting outward in a radial direction, and a second projection located at the distal end and projecting outward in the radial direction, in which a projecting amount of the second projection projecting outward in the radial direction with respect to the cylindrical outer peripheral part is smaller than that of the first projection, the wound body comprises a core body having a cylindrical shape, and the long sheet wound around an outer periphery of the core body, the core body comprises a cylindrical inner peripheral part having one end and an other end, the cylindrical inner peripheral part comprises a first recess part located at the one end and recessing into the core body in the radial direction, and a second recess part located to extend from the one end to the other end and recessing into the core body in the radial direction, in which a recessing amount of the second recess part recessing into the core body in the radial direction with respect to the cylindrical inner peripheral part is smaller than that of the first recess part, the core body is mountable on an outer periphery of the support shaft from the one end side of the core body and from the distal end side of the support shaft, the support shaft and the core body are integrally rotatable around the central axis by engagement of the first projection with the first recess part in a state where the core body is mounted on the outer periphery of the support shaft, a circumferential position of the first projection around the central axis is aligned with a circumferential position of the first recess part around the central axis by engagement of the second projection with the second recess part when the core body is mounted on the outer periphery of the support shaft, the second recess part comprises a leading part that is configured to lead the second projection, the leading part is configured to lead the second projection to allow the circumferential positions of the first projection and the first recess part around the central axis to be aligned with each other when the core body is mounted on the outer periphery of the support shaft, the second recess part comprises a guide part that guides the second projection, the guide part is located closer to the other end of the core body than the leading part, and is configured to guide the second projection to allow the circumferential positions of the first projection and the first recess part around the central axis to be kept in alignment with each other when the core body is mounted on the outer periphery of the support shaft, the cylindrical outer peripheral part of the support shaft comprises a third projection that is located at an intermediate position between the proximal end of the support shaft and the distal end of the support shaft, and that projects outward in the radial direction, the third projection is located at a same position as the second projection in a circumferential direction around the central axis, a projecting amount of the third projection projecting outward in the radial direction with respect to the cylindrical outer peripheral part of the support shaft is the same as that of the second projection, and the third projection is guided by the guide part to allow the circumferential positions of the first projection and the first recess part around the central axis to be kept in alignment with each other when the core body is mounted on the outer periphery of the support shaft.

21. The combination of the wound body and the medicine packing apparatus according to claim 20, wherein the support shaft comprises a movable part that is located at the first projection, that is configured to project outward in the radial direction from the core body in the state where the core body is mounted on the outer periphery of the support shaft, that is disposed to be movable in an axial direction of the central axis, and that is biased in a direction from the proximal end of the support shaft toward the distal end of the support shaft, the core body comprises a cutout that is located at a same position as the first recess part in a circumferential direction of the core body in the one end of the core body, that has a cutout shape extending from an end face of the one end of the core body toward the other end of the core body, and that is configured to allow the movable part to enter the cutout, and the medicine packing apparatus is configured to stop an operation of the medicine packing apparatus when the movable part enters the cutout.

* * * * *